United States Patent
Polt et al.

(10) Patent No.: US 7,803,764 B2
(45) Date of Patent: Sep. 28, 2010

(54) AMPHIPATHIC GLYCOPEPTIDES

(75) Inventors: Robin L. Polt, Tuscon, AZ (US); Edward Bilsky, Biddeford, ME (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 466 days.

(21) Appl. No.: 10/594,515

(22) PCT Filed: Mar. 25, 2005

(86) PCT No.: PCT/US2005/010233

§ 371 (c)(1),
(2), (4) Date: Sep. 28, 2006

(87) PCT Pub. No.: WO2005/097158

PCT Pub. Date: Oct. 20, 2005

(65) Prior Publication Data

US 2008/0207492 A1    Aug. 28, 2008

Related U.S. Application Data

(60) Provisional application No. 60/641,492, filed on Jan. 5, 2005, provisional application No. 60/583,257, filed on Jun. 25, 2004, provisional application No. 60/557,740, filed on Mar. 29, 2004.

(51) Int. Cl.
*A61K 38/00* (2006.01)
*A61K 38/14* (2006.01)
*C07K 9/00* (2006.01)

(52) U.S. Cl. ............... 514/8; 514/12; 514/13; 514/14; 530/302; 530/322; 530/324; 530/326; 530/327

(58) Field of Classification Search ............. None
See application file for complete search history.

(56) References Cited

U.S. PATENT DOCUMENTS

| 5,091,367 A | * | 2/1992 | Konig et al. ............ 514/15 |
| 6,525,021 B1 | * | 2/2003 | Wagstaff et al. ........... 514/8 |
| 2002/0127652 A1 | * | 9/2002 | Schambye et al. ......... 435/69.4 |

OTHER PUBLICATIONS

Bulet et al. Enlarged scale chemical synthesis and range of activity of drosocin . . . European Journal of Biochemistry. 1996, vol. 238, pp. 64-69.*

Egleton et al. Biousian glycopeptides penetrate the blood-brain barrier. Tetrahederon: Asymmetry. Jan. 8, 2005, vol. 16, pp. 65-75.*

Palian et al. Alpha-Helical Glycopeptide Analgesics: Beta-Endorphin Mimics with Good in vivo Potency. Peptides: The Wave of the Future. American Peptide Society, 2001, pp. 499-501.*

(Continued)

*Primary Examiner*—Jeffrey E Russel
(74) *Attorney, Agent, or Firm*—Oblon, Spivak, McClelland, Maier & Neustadt, L.L.P.

(57) ABSTRACT

Amphipathic glycopeptides, the amino acid sequence of which comprises an N-terminal opioid message sequence, a C-terminal helical address sequence, and a linker sequence between the message sequence and the helical address sequence, where the C-terminal helical address sequence has a length of nine amino acids, and at least one of the amino acid residues of the peptide is glycosylated. The peptides are useful for relieving pain, providing analgesia and treating anxiety, depression, obesity, anorexia nervosa, phobias, schizophrenia, Parkinson's disease and Alzheimer's disease.

32 Claims, 18 Drawing Sheets

OTHER PUBLICATIONS

Polt et al. Glycopeptide analgesics. 2001. Drugs of the Future. vol. 26, No. 6, pp. 561-576.*
Dhanasekaran et al. Glycopeptides Related to Beta-Endorphin Adopt Helical Amphipathic Conformations in the Presence of Lipid Bilayers. Journal of the American Chemical Society. Mar. 24, 2005, vol. 127, No. 15, pp. 5435-5448.*
Polt et al. Glycopeptide analgesics . . . Abstracts of Papers, 227th ACS National Meeting. Mar. 28-Apr. 1, 2004. Abstract ORGN-278.*
Egleton et al. Physiochemical analysis and CNS bioavailability of opioid amphipathic glycopeptides. FASEB Journal. Mar. 4, 2005, vol. 19, No. 4, Suppl. S, Part 1, p. A510, Abstract 310.7.*

Mitchell, Scott A. et al.,"Solid-Phase Synthesis of O-Linked Glykopeptide Analogues of Enkephalin", J. Org. Chem., vol. 66, No. 7, pp. 2327-2342, 2001.
Palian, Michael M. et al.,"Glycopeptide-Membrane Interactions: Glycosyl Enkephalin Analogues Adopt Turn Conformations by NMR and CD in Amphipathic Media", J. Am. Chem. Soc., vol. 125, No. 19, pp. 5823-5831, 2003.
Bilsky, Edward J. et al.,"Enkephalin Glycopeptide Analogues Produce Analgesia with Reduced Dependence Liability", Journal of Medicinal Chemistry, vol. 43, No. 13, pp. 2586-2590, 2000.

* cited by examiner a)

b)

c)

SEQUENCE LISTING

<160> NUMBER OF SEQ ID NOS: 17

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 1

Tyr Gly Gly Phe Met
  1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Gly Gly Phe Leu
  1               5

<210> SEQ ID NO 3
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Gly Gly Phe Met Thr Ser Gln Thr Pro Leu Val Thr Thr Leu Phe
  1               5                  10                  15

Lys Asn Ala Ile Ile Lys Asn Ala Tyr Lys Lys Gly Glu
                 20                  25

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Gly Gly Phe Leu Arg Lys Tyr
  1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Gly Gly Phe Leu Arg Lys Tyr Pro
  1               5

<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Gly Gly Phe Met Arg Arg Val Gly Arg Pro Glu Trp Trp Met Asp
  1               5                  10                  15

Tyr Gln Lys Arg Tyr Gly Gly Phe Leu
```

```
<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Glu Val Leu Gly Lys Arg Tyr Gly Gly Phe Met
 1               5                   10

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Phe Gly Gly Phe Leu Arg Arg Ile Arg Pro Lys Leu Lys Trp Asn Asn
 1               5                   10                  15

Gln

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Tyr Gly Gly Phe Leu Arg Arg Ile Arg Pro Lys Leu Lys Trp Asp Asn
 1               5                   10                  15

Gln

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Gly Gly Phe Leu Arg Arg Ile Arg Pro Lys Leu Lys
 1               5                   10

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Gly Gly Phe Leu Arg Arg Gln Phe Lys Val Val Thr
 1               5                   10

<210> SEQ ID NO 12
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr Pro Phe Pro
  1

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Pro Phe Pro Gly Pro Ile
  1               5

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Pro Trp Phe
  1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Pro Phe Phe
  1

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Pro Leu Asp Leu Phe
  1               5

<210> SEQ ID NO 17
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 17

Tyr Gly Gly Phe
 1
```

AMPHIPATHIC GLYCOPEPTIDES

CROSS-REFERENCE TO RELATED APPLICATIONS

This application claims priority to U.S. application Ser. Nos. 60/557,740, filed on Mar. 29, 2004, 60/583,257, filed on Jun. 25, 2004, and 60/641,492 filed on Jan. 5, 2005, each of which is incorporated herein by reference.

STATEMENT REGARDING FEDERALLY SPONSORED RESEARCH OR DEVELOPMENT

The invention described herein was supported by ONR-N00014-02-1-0471 and NSF-CHE9526909. Therefore, the Government may have certain rights to this invention.

BACKGROUND OF THE INVENTION

1. Field of the Invention

The present invention relates to glycopeptides which are amphipathic. The glycopeptides of the present invention are capable of crossing the blood-brain-barrier (BBB). As a result, the glycopeptides for treating a variety of neurological and behavioral disorders.

2. Description of the Background

Endogenous opioid peptides, lumped together under the generic term endorphins, have been the subject of intense study since their discovery in the mid 1970's.[1] Neuropeptides have the potential for extremely selective pharmacological intervention with fewer side effects. If these naturally occurring opioid peptides and their derivatives could be rendered permeable to the blood-brain barrier (BBB), then a new vista of psychopharmacology would be opened to exploration. After three decades of research, many potent and selective opioid agonists have been developed, and stability problems have been largely overcome. The principal remaining problem that prevents the use of opioid peptides as drugs is poor bioavailability, which is due to poor penetration of the BBB.[2] The BBB is composed of endothelial cells in the cerebrovascular capillary beds.[3] The BBB acts as a barrier to undesired chemical substances, and admits vital nutrients for proper function of the CNS.[4] The flow is bi-directional, allowing for export of materials from the CNS (efflux transport) and the import of materials from the blood (influx transport). The BBB represents not only a physical obstacle, but a metabolic one as well, possessing both oxidative enzymes and peptidases such as aminopeptidase, arylamidase and enkephalinase. Thus, metabolically unstable substances (e.g. peptides) are generally degraded before they reach the CNS. It should also be noted that entry to the CNS does not guarantee that a drug will accumulate in useful concentrations, as many peptides are rapidly exported back to the bloodstream.[5] Several strategies have been reported to overcome the BBB penetration problem, including substitution of unnatural amino acids,[6] the use of conformational constraints,[7] and the addition of lipophilic side chains or other transport vectors.[8] Glycosylation has proven to be a successful methodology to improve both the stability and bioavailability of short peptide "messages" by incorporation of the peptide pharmacophore into a glycopeptide.[9] Previous BBB penetration studies with opioid glycopeptide agonists based on enkephalins have shown up to 3-fold increases in the rate of brain delivery of these compounds compared with the unglycosylated parent peptides.[10] Recent studies with glycopeptides in artificial membrane systems indicate that amphipathicity of the glycopeptides is an important factor in BBB penetration.[11] In addition, there is evidence that suggests that the type of glycosylation can alter tissue distribution patterns,[12] BBB penetration,[13] and peptide/receptor interactions.[11,14]

Endogenous Opioid Peptides. The endogenous neuropeptide β-endorphin is a 31 residue naturally occurring opioid peptide agonist that binds to μ and δ receptors. Its N-terminal 5 residues are identical to the Met-Enkephalin sequence, and may be considered to be the pharmacophore. It was shown some time ago that the C-terminal region of β-endorphin has an amphipathic α-helical structure that plays a role in the receptor binding and opioid agonism,[15] and may induce resistance to proteolysis.[16] According to Schwyzer, the N-terminal sequence is the essential "message," and the C-terminal helical region is the "address" that limits delivery of the message to a subset of otherwise available opioid receptors.[17] Kaiser and co-workers proposed that β-endorphin consists of the Met-enkephalin peptide sequence at the N-terminus, a hydrophilic linker region from residues 6 through 12, and an amphiphilic helical region between the helix breaker residues Pro(13) and Gly(30).[18] This was later proven by synthesizing a number of β-endorphin mimics with artificial C-terminal helical regions with amphipathic character.[19] These de novo amphipathic helices were non-homologous to the β-endorphin C-terminal region, and they were shown to be largely α-helical by CD measurements. These hybrid structures showed good opioid agonism in vitro when compared to β-endorphin. These studies strongly suggested that the amphipathicity of the C-terminal helix plays a key role in the selectivity of these compounds, rather than the identity of specific amino-acids present in the C-terminal.[20] Dynorphin A (1-17) is also an endogenous opioid peptide, but it binds preferentially to the κ opioid receptor and has an N-terminal message segment identical to Leu-Enkephalin.[21] It has been suggested that an address sequence in the C-terminal region imparts selectivity for κ receptors.[22] Dynorphin A adopts an extended and/or random coil structure when subjected to structural analysis by various spectroscopic measurements.[23] A 2D $^1$H-NMR study in DPC micelle shows that Dynorphin A(1-17) contains a less ordered N-terminal segment, a well defined α-helix segment spanning between Phe(4) and Pro (10) or Lys(11), and a β-turn from Trp(14) to Gln(17).[24] Based on NMR results, the authors concluded that both the α-helix and the C-terminal β-turn are due to dynorphin-micelle interactions, and may be important structural features of the full-length peptide when bound to the cell membrane in vivo. Studies by Luna[25] also support the notion that a helical structure in the message segment of Dynorphin A(1-17) is significant. The biological importance of helical C-terminal address segments in larger opioid peptides has been further supported by the recent work by Kyle and co-workers.[26] They successfully synthesized several potent nociceptin (NC) peptide analogs exploiting the α-helix-promoting residues α-aminoisobutyric acid (Aib) and N-methyl alanine (MeAla) at the C-terminus of NC. Nociceptin is the endogenous ligand for the recently identified opioid receptor-like 1 receptor (ORL-1). Thus, it seems logical to approach the design of opioid agonist β-endorphin or dynorphin peptide analogs by combining C-terminal amphipathic helical address segments that can also promote BBB penetration by virtue of glycosylation.

SUMMARY OF THE INVENTION

It is an object of the invention to provide glycopeptides which are amphipathic. These glycopeptides are essentially non-helical in pure water but adopt a helical structure in the presence of a lipid bilayer. The presence of the carbohydrate permits the helical structure to leave the membrane to form a water soluble random coil, so that the glycopeptide does not remain embedded in the membrane, but can move from membrane to membrane, reforming the helical amphipathic structure each time. As a result of this structural dynamic, the glycopeptides of the present invention are capable of crossing the blood-brain-barrier (BBB). As a result, the glycopeptides for treating a variety of neurological and behavioral disorders.

Thus, the present invention provides an amphipathic glycopeptide, wherein the glycopeptide comprises at least 9 amino acid residues, and wherein at least one of the amino acid residues is glycosylated.

The present invention also provides a pharmaceutical composition comprising the glycopeptide and at least one pharmaceutically acceptable carrier and/or excipient.

The present invention also provides a method of relieving pain, comprising administering an effective amount of the glycopeptide to a subject in need thereof.

The present invention also provides a method of providing analgesia, comprising administering an effective amount of the glycopeptide to a subject in need thereof.

In addition, the present invention provides a method of treating anxiety, depression, obesity, anorexia nervosa, phobias, schizophrenia, Parkinson's disease and Alzheimer's disease, comprising administering an effective amount of the glycopeptide to a subject in need thereof.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

The figure numbers are the original numbers and have not been renumbered

DETAILED DESCRIPTION OF THE INVENTION

Figure 1:
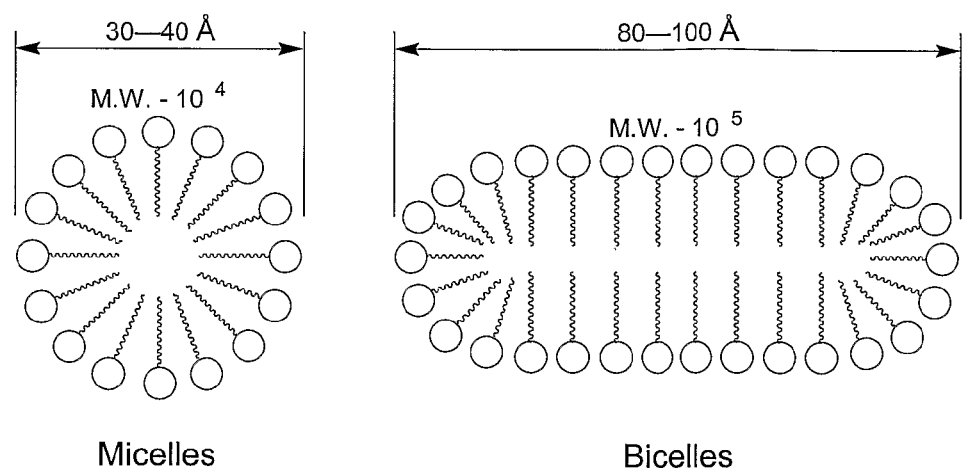
FIG. 1. Membrane mimics used in CD and NMR studies. Bicelles have much less membrane curvature than micelles, have a true fluid bilayer, and are more predictive of the membrane-bound glycopeptide structure.

As discussed above, the present invention provides an amphipathic glycopeptide, wherein the glycopeptide comprises at least 9 amino acid residues, and wherein at least one of the amino acid residues is glycosylated. As used herein, the term "amphipathic" as used herein has the same meaning as used generally in the field of peptide and protein chemistry. Thus, the glycopeptides of the present invention possess both hydrophilic and hydrophobic functional groups. In particular, when the glycopeptides adopt a helical conformation, as discussed in detail herein, the sequence displays a hydrophobic surface and a hydrophilic surface, as discussed in detail below.

In a preferred embodiment of the present invention, the glycopeptide adopts a helical conformation in the presence of a lipid bilayer, which reflects its conformation at the endothelial layer of the BBB. The glycopeptides also adopt a helical conformation in the presence of TFE-water mixtures, micelles and/or bicelles. Helicity can be measured by circular dichroism, by NMR, and even by reversed phase HPLC. As measured these ways, the glycopeptide has a helicity of at least 10%. In preferred embodiments, the glycopeptide has a helicity of at least 15%, 20%, 30%, 40%, 50%, 60%, 70%, 80%, 85% or 90%.

In another embodiment, the glycopeptide is substantially non-helical in water in the absence of a lipid bilayer. Helicity can be measured by circular dicliroism. As measured this way, the glycopeptide has a helicity of at most 5%. In preferred embodiments, the glycopeptide has a helicity of at most 4%, 3%, 2% or 1%. In fact, the degree of helicity may be below the level of detection of the particular assay technique.

In an especially preferred embodiment, the glycopeptide is substantially non-helical in water in the absence of a lipid bilayer and adopts a helical conformation in the presence of a lipid bilayer. Preferred embodiments of such a compound are as described just above.

As a result of this conformation dynamic, the glycopeptides of the present invention may be capable of crossing the blood-brain-barrier. In preferred embodiments, the glycopeptides have a BBB uptake of 0.001 to 0.5 microliters per min per gram of cortex (see Table 1 below). This range includes all specific ranges and subranges therebetween, such as 0.002, 0.005, 0.01, 0.02, 0.05, 0.1, 02 and 0.4. In another embodiment, the glycopeptides are soluble in water.

In a preferred embodiment of the present invention, the amino acid sequence of the glycopeptide comprises an N-terminal opioid message sequence, a C-terminal address sequence, and a linker sequence between the message sequence and the address sequence. A wide variety of opioid message sequences and address sequences are well-known and may be used in the present invention, in addition to non-opioid message sequences with the same address sequences. Suitable message sequences include the following:

| Delta-Selective Message Sequences | |
|---|---|
| Met-Enkephalin | Y-G-G-F-M (SEQ ID NO: 1) |
| DSLET | Y-dS-G-F-L-S |
| DTLET | Y-dT-G-F-L-T |
| DSTBULET | Y-dS(OtBu)-G-F-L-T |
| DPDPE | Y-dPen-G-F-dPen (SS) |
| Deltorphin | Y-dM-F-H-L-M-D-CONH$_2$ |

| Mu- and Kappa-Selective Message Sequences | |
|---|---|
| Leu-Enkephalin | Y-G-G-F-L (SEQ ID NO: 2) |
| LYM-147 | Y-dA-G-MeF |

| Mu- and Kappa-Selective Message Sequences | |
|---|---|
| DAMGO | Y-dA-G-MeF-NH—CH$_2$CH$_2$OH |
| Dermorphin | Y-dA-F-G-Y-P-S |
| beta-Endorphin | Y-G-G-F-M-T-S-Q-T-P-L-V-T-T-L-F-K-N-A-I-I-K-N-A-Y-K-K-G-E (SEQ ID NO: 3) |
| alpha-neo-Endorphin | Y-G-G-F-L-R-K-Y (SEQ ID NO: 4) |
| beta-neo-Endorphin | Y-G-G-F-L-R-K-Y-P (SEQ ID NO: 5) |
| Peptide E | Y-G-G-F-M-R-R-V-G-R-P-E-W-W-M-D-Y-Q-K-R-Y-G-G-F-L (SEQ ID NO: 6) |
| Peptide F | G-G-E-V-L-G-K-R-Y-G-G-F-M (SEQ ID NO: 7) |
| Niociceptin (FQ) | F-G-G-F-L-R-R-I-R-P-K-L-K-W-N-N-Q (SEQ ID NO: 8) |
| Dynorphin A (1-17) | Y-G-G-F-L-R-R-I-R-P-K-L-K-W-D-N-Q (SEQ ID NO: 9) |
| Dynorphin A (1-13) | Y-G-G-F-L-R-R-I-R-P-K-L-K (SEQ ID NO: 10) |
| Dynorphin B | Y-G-G-F-L-R-R-Q-F-K-V-V-T (SEQ ID NO: 11) |
| Morphiceptin | Y-P-F-P (SEQ ID NO: 12) |
| beta-Casomorphin | Y-P-F-P-G-P-I (SEQ ID NO: 13) |
| Endomorphin-1 | Y-P-W-F (SEQ ID NO: 14) |
| Endomorphin-2 | Y-P-F-F (SEQ ID NO: 15) |
| Rubiscolin-6 | Y-P-L-D-L-F (SEQ ID NO: 16) |

In the sequences listed above, dA, dS, dT, dM, dPen represent D-alanine, D-serine, D-threonine, D-methionine and D-penicilimine, respectively.

Regarding the linker sequence, in principle, any relatively short sequence of amino acids, or relatively short sequence of carbon atoms can serve as a linker. If one wishes to have the amphipathic helix transport sequence overlap with the message sequence, a short, non-demanding linker such as a single glycine, or two glycines may be used. If one wishes to have a moderately stable amphipathic helix transport sequence, then a helix-destabilizing amino acid such as a single proline may be used. If one wishes the helical address region to terminate, and not overlap with the message, then a helix-breaker such as beta alanine, or two prolines, or a longer sequence can be used. The linker can be varied to suite the particular message, and has been shown to have a large impact on the BBB transport rates. The optimum linker for a given address and message can be determined using routine experimentation.

In one embodiment, the glycopeptide comprises at least 10 amino acid residues. In other embodiments, the glycopeptide may contain at least 11 to at least 50 amino acid residues. This range includes all specific values and subranges therebetween. For example, the glycopeptide may contain at least 11, 12, 14, 15, 17, 19, 20, 25, 30, 35, 40 or 45 amino acid residues. In preferred embodiments the glycopeptide may contain at most 60 amino acid residues. The sequence may also comprise at most 55, 50 or 45 amino acid residues in other embodiments. Thus, glycopeptide of the present invention may have an amino acid sequence that is 10-60 residues in length. This range includes all specific values and subranges therebetween, such as 12, 15, 20, 25, 30, 40 and 50 amino acid residues.

In one embodiment, the glycopeptide is a glycosylated enkephalin. In another embodiment, the glycopeptide is a glycosylated endorphin.

The glycopeptide may have the N-terminal sequence Y-a-G-F-, T-t-G-F-, Y-t-G-F-L-, Y-t-G-F-L-P-, Y-t-G-F-L-βA-, or Y-t-G-F-L-G-G-. The symbols "a", "t" and "βA" represent D-alanine, D-threonine and β-alanine, respectively. Unless noted otherwise, a single amino acid depicted in lower case refers to the D-amino acid. Other suitable N-terminal sequences include Y-G-G-, Y-G-G-F- (SEQ ID NO: 17), Y-m-F-, Y-m-F-H-, Y-a-F-, Y-a-F-G-, Y-P-F, Y-P-F-P- (SEQ ID NO: 12), Y-P-F-F- (SEQ ID NO: 15), Y-P-W, and Y-P-W-F- (SEQ ID NO: 14). In addition, many non-opioid sequences may be used in the present invention, including sequences from corticotropin releasing factor (CRF), lutenizing hoinione (LH), human chorionogonadotropin (hCG), follicle stimulating hormone (FSH), vasoactive intestinal peptide (VIP), bradykinin, vasopressin, neurokinins, substance P, prolactin, and many other hypothalamic peptide hormones.

As used herein, the term "glycosylated" means that an amino acid residue is functionalized with a glycosyl group. A glycosyl group is composed of saccharide units. These terms are well-known in the field of peptide and protein chemistry and have such meanings as used herein. In preferred embodiments, the glycosyl group has at most 8 saccharide units. More preferably, the glycosyl group has at most 4 saccharide units. In another embodiment, the glycosyl group is at most a disaccharide, i.e., the glycosyl group has at most 2 saccharide units. Thus, the total number of saccharide units may be from 1 to 8, inclusive of all specific values and ranges therebetween. Example of glycosyl groups include β-D-glucose, β-maltose, β-lactose, β-melibiose and β-maltotriose. Other examples include sucrose, trehalose, saccharose, maltose, cellobiose, gentibiose, isomaltose and primeveose. Other glycosyl groups include galactose, xylose, mannose, manosaminic acid, fucose, GalNAc, GlcNAc, idose, iduronic acid, glucuronic acid and sialic acid.

In one embodiment of the invention, one amino acid residue is glycosylated. In another embodiment, two amino acid residues are glycosylated. In other embodiments, the glycopeptide may have 3 or 4 or more glycosylated amino acid residues.

In a preferred embodiment, the glycopeptide comprises at least one serine residue that is glycosylated. In another preferred embodiment, the glycopeptide comprises 2 serine residues that are glycosylated. In one specific embodiment, the glycopeptide contains one serine glucoside residue. In another specific embodiment, the glycopeptide contains 2 serine glucoside residues.

Suitable methods for preparing glycopeptides are well-known. The well-known methods of solid phase peptide synthesis can be used to prepare the glycopeptides of the present invention. It is preferred that the glycosyl group be linked to the amino acid sequence by an O-linkage to a side chain in the address segment of the sequence. See Tetrahedron Asymmetry 16, 65-75 (2005), incorporated herein by reference, and U.S. Pat. No. 5,727,254.

In a particularly embodiment of the present invention, the glycopeptides of the present invention is selective for the delta opioid receptor, mu opioid receptor or kappa opioid receptor. In this embodiment, the glycopeptides are receptor agonists. In fact, any g-protein coupled receptor (GPCR) could be a target for glycopeptides designed using these concepts.

As a result, the glycopeptides of the present invention may be useful for treating a variety of neurological and/or behavioral disorders that are mediated by those receptors. Thus, the glycopeptides may be used for relieving pain by administering an effective amount of the glycopeptide to a subject in need thereof. The glycopeptides may also be used to provide analgesia by administering an effective amount to a subject in need thereof. The glycopeptides may also be used to treat anxiety, depression, obesity, anorexia nervosa, phobias, schizophrenia, Parkinson's disease and Alzheimer's disease by administering an effective amount to a subject in need thereof.

The subject is preferably a human. The subject may also be a non-human animal, especially a mammal. Suitable animals include mice, rats, dogs, horses, sheep, and monkeys.

The present invention also includes a pharmaceutical composition comprising the glycopeptide and at least one pharmaceutically acceptable carrier and/or excipient. The glycopeptides of the present invention may be prepared for pharmaceutical administration by methods and excipients generally known in the art (Remington's Pharmaceutical Sciences, E. W. Martin). Carriers and excipients may include water, pH buffers, such as citrate or phosphate buffers, 'wetting agents' such as Tweens or other detergents, salts such as sodium chloride, reducing agents such as thiols, sugars, such as dextrose, lactose, sucrose and the like, glycerol, glycol, oils, preservatives, antimicrobials, etc. The composition may be prepared as a liquid, powder, solid or in gel form for administration. Administration may be via parenteral routes, such as intravenous, intraperitoneally or subcutaneous, oral, nasal, inhalation, rectally via suppositories or other known routes of administering drugs. Dosages and administration schedules are readily determined by those skilled in the pharmacology. A suitable dosage range for the glycopeptides is 0.001 microgram per kilo to 30 milligrams per kilo of body weight.

Glycopeptide Design Principles. Three series of glycosylated β-endorphin analogs have been designed and synthesized for study. The peptide sequences were not homologous to β-endorphin, but the C-terminal regions were designed to produce amphipathic helix conformations, and bear one or more serine glycosides. A complete blood-brain barrier study of these compounds in mice will be published separately,[i] but some of the most salient BBB results will be presented here, along with opioid binding and functional assays. It is noteworthy that some of the much longer endorphin glycopeptide analogs penetrate the mouse BBB at higher rates than the much shorter enkephalin glycopeptide analogs. In this study, we will focus on the design and conformational analysis of representative β-endorphin glycopeptide analogs in water, TFE-water mixture, SDS micelles and bicelles determined by 2D-$^1$HNMR and circular dichroism (CD). The organic solvent trifluoroethanol (TFE) has traditionally been used to promote secondary structure formation.[ii] Later, the use of detergent micelles was proposed to study peptide-membrane interactions.[iii] Recently, in order to better mimic the flatter membrane environment, the use of phospholipid bicelles was proposed, and is gaining momentum because of its advantages over organic solvents and micelles.[iv] The bicelles used in the NMR studies are disk-shaped aggregates formed by mixing long-chained phospholipids, such as dimyristoylphosphatidylcholine (DMPC) which form a bilayer domain disk, along with short-chained surfactant phospholipids, such as dihexanoylphosphatidylcholine (DHPC) that seal the edges of the bilayer.[30b,v] Unlike micelles, which show extreme positive curvature, the phospholipid bicelles constitute a true fluid membrane bilayer segment with a very low curvature (FIG. 1). It has been shown that while some membrane-bound enzymes lose their activity in micellar solution, activity is often retained when bound to phospholipid bicelles.[vi] It has also been shown previously that Met-enkephalin shows a different conformational ensemble in the presence of the more fluid bicelles than in a micelle environment.[vii] Conformational studies of cell-penetrating peptides in SDS micelle and bicelle systems show that these peptides adopt very similar structure in both systems, but the position of the peptides in a micelle differs significantly from the position in the phospholipid bilayer.[viii] Thus, in order to understand the behavior of the glycopeptides that traverse the BBB, it is important to study the conformational properties of the glycopeptides in TFE-water mixtures as well as in membrane mimicking micelles and bicelles.

Robert Schwyzer pointed out the importance of the membrane in peptide-receptor interactions with the development of his "membrane compartment theory." According to this theory, the lipid phase of a cellular membrane acts as a matrix for the receptor and the ligand.[14] Max Delbruck performed a theoretical study of receptor-ligand interactions in the context of "membrane compartmentalization."[35] He found that a 2D search for a receptor was much more efficient than a 3D search for a receptor, and suggested that the initial interaction was adsorption of a ligand to the membrane. Membrane insertion can also induce a specific conformation of the ligand, different from its solution conformation, and this membrane-bound conformation is likely to be the bioactive conformation.

Helices are the most commonly occurring secondary structural elements in globular proteins, accounting for one-third of all the residues.[36] In 1974, Segrest and co-workers first theorized the amphipathic (a.k.a. amphiphilic) helix as a unique structure/function structural motif of proteins involved lipid interaction.[37] It is estimated that over 50% of all α-helices in nature are amphipathic.[38] These proteins are unique in that they possess hydrophobic and hydrophilic regions, either by primary structure (having hydrophilic N-terminus and hydrophobic C-terminus) or by secondary structure, with polar residues pointing one face and the nonpolar residues on the opposite side. This allows them to "float" in cell membranes, exposing the hydrophilic side to the aqueous exterior of the cell and the hydrophobic side to the lipophilic membrane. Several functional properties are associated with amphipathic helices, which include lipid association, membrane perturbation in the form of fusion or lysis, hormone-receptor catalysis, transmembrane signal transduction, regulation of kinase-calmodulin signal transduction, and transmembrane helical bundle formation.[39] Amphipathic cell penetrating peptides (CPP) have been used for drug delivery into the cytosol.[40] These Class L (e.g. lytic) amphipathic helices are believed to aggregate on the cell surface, followed by rotation to produce pores through the lipid bilayer. This would not be a good scenario for penetration of the BBB. Rather, Class A (e.g. apolipoprotein) amphipathic helices, which do not aggregate or form pores seem to be desired in order to participate in endocytotic events at the endothelial layer. Class A amphipathic helices will prevent the glycopeptides from entering the cytosol, or inserting too deeply into the membrane—which can become irreversible events in the context of traversing the BBB. Thus, the residues that form the hydrophilic face of the amphipathic helices used in these studies have been chosen to occlude a large angle, close to 180°, and should provide Class A amphipathic helices that "ride high" in the membrane, and are less likely to aggregate to form pores.

Figure 2:
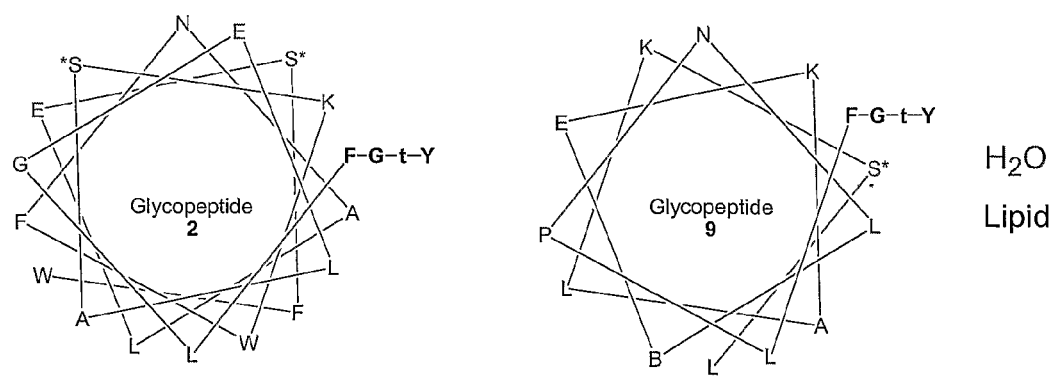
FIG. 2. To design the $1^{st}$-$3^{rd}$ generation glycopeptides they were illustrated as amphipathic α-helical wheels (2 and 9 are shown). The expected membrane position is shown as a line.
Figure 3:
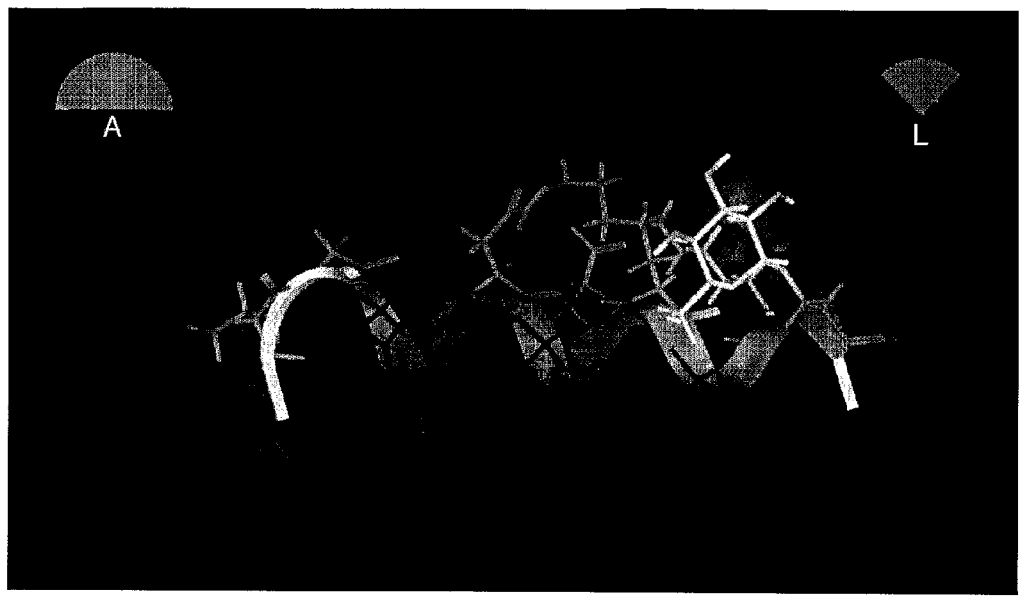
FIG. 3. Glycopeptide 9 is illustrated as a "perfect" amphipathic helix (N-terminal message segment to the left), with a calculated Connolly surface. Idealized "Class A" and "Class L" amphipathic helices are shown as Edmund diagrams (end view).
Figure 4:
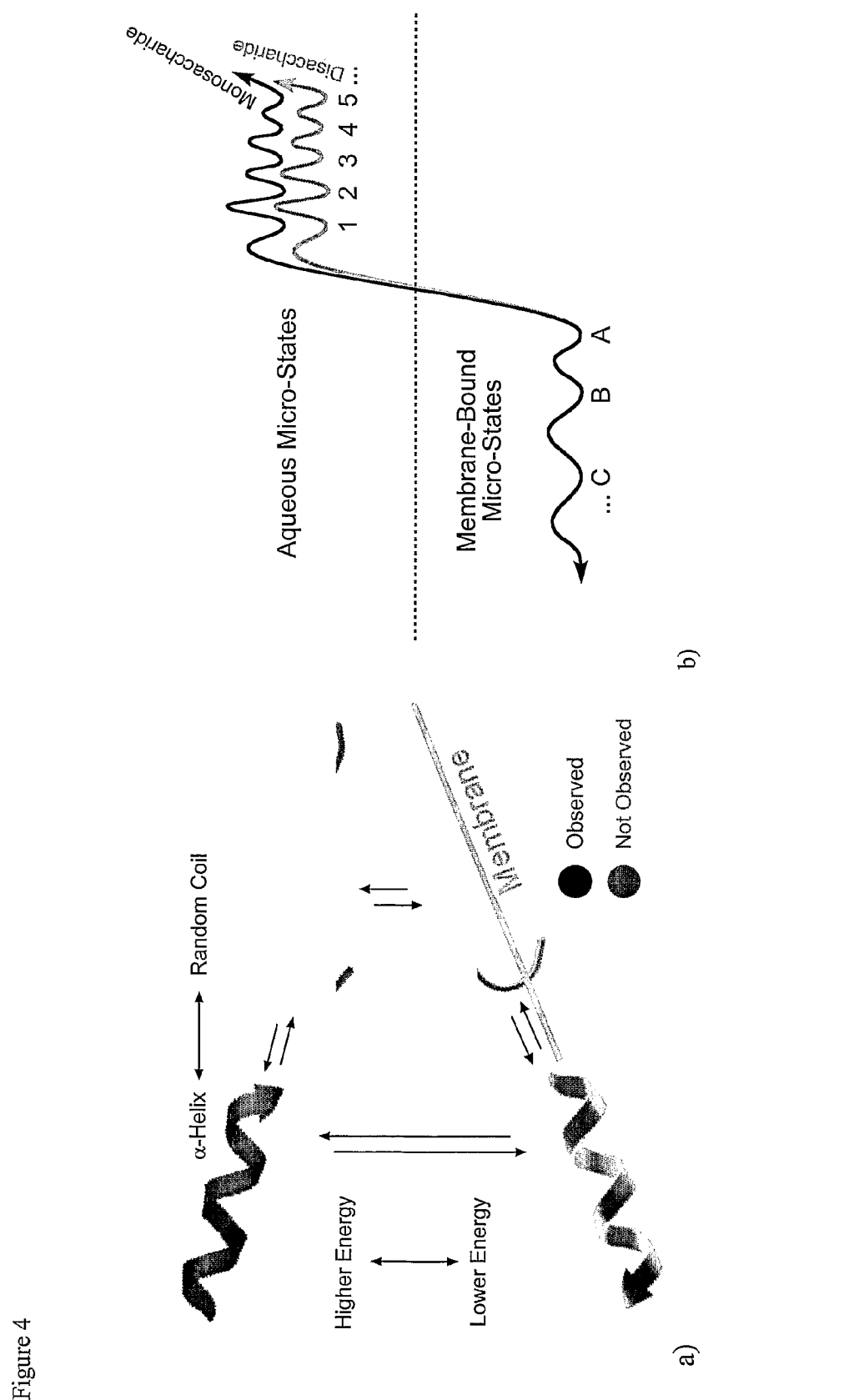
FIG. 4. a) Changes in the conformational ensemble are promoted by the membrane. The solution form of the α-helix may be viewed as high energy intermediate leading to interaction of the membrane, or the membrane may be viewed as a catalyst leading to helix formation. b) Each glycopeptide has a small set of low energy membrane-bound micro-states (A, B, C . . . ), as well as a much larger set of higher energy solution microstates (1, 2, 3 . . . ).
Figure 5:
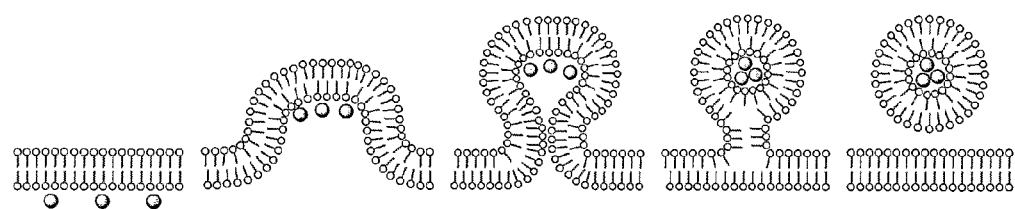
FIG. 5. Putative endocytotic transport mechanism. It is hypothesized that the amphipathic glycopeptides (3 small spheres at left) can adsorb to the endothelium of the BBB on the blood side, and undergo endocytosis to form vesicles. After the vesicles find their way to the brain side of the endothelial layer of cells, exocytosis can deliver the glycopeptides to the central nervous system.

The helical glycopeptides in these studies were designed in accord with classic studies of helix formation[41] combined with a simple Edmundson wheel approach to introducing amphipathicity (FIG. 2). Molecular mechanics calculations also supported helical, amphipathic structures for the glycopeptides (FIG. 3). Solvent-accessible areas (Connolly surface) labeled different colors for hydrophobic and hydrophilic residues suggested that these molecules could exist as Class A amphipathic helices when in a membrane environment, and it was our hope that we could achieve optimal on and off rates to achieve penetration of cellular barriers by transcytosis.[10,11]

The same δ-selective DTLES message segment[42] used in previous work has been used throughout these studies. The message and address segments were connected via a peptide linker in an effort to "break" the helix. Three sets of glycopeptides were designed with the common message segment YtGFL with differing linker and amphipathic helix address segments (Table 1). The $1^{st}$ generation of helical glycopeptides (1-4) have a common Gly linker, but differ in the address segment sequence length (simple truncation). One or two glycosylation sites were incorporated to promote detachment of the amphipath from the membrane. Of these four $1^{st}$ generation glycopeptides, only glycopeptide 2 showed any appreciable water solubility. The $2^{nd}$ generation glycopeptides (5-8) incorporated fewer hydrophobic regions and a third glycosylation site in an effort to make them more water soluble. All of the $2^{nd}$ generation helices were, indeed, water soluble. In both the $1^{st}$ and $2^{nd}$ generation glycopeptides the Gly linker was ineffective in terminating the helix, which propagated into the YtGFL message. In the $3^{rd}$ generation of helical glycopeptides (9-12) three different linkers, Pro, β-Ala, Gly-Gly, were used with the same helical segment, which was much shorter, and contained Aib, a residue known to promote helix formation. Neither Pro nor Gly-Gly was very effective in terminating the helix. The length of the C-terminal helical segment was fixed at nine residues in length in the $3^{rd}$ generation design, sufficient to form two complete α-helical turns. None of the C-terminal helical address segments have any sequence homology to natural β-endorphin or dynorphin C-terminal segments. Since the stabilizing forces involved in helix formation are local, such as a regular network of internal hydrogen bonds, electrostatic interactions between charged side-chains, helix design is easier than β-sheet design.[43] Strategies previously used to create short stable helical peptides include: i) the incorporation of helix stabilizing Ala residues,[44] ii) use of α-methylated amino acids,[45] iii) adding salt bridges between residues separated by one α-helical turn,[46] iv) incorporating covalent macrocycles,[47] and v) adding nonpeptide templates to initiate helix formation.[48] Thus, our design is based purely on protein folding principles and amino acid characteristics (e.g. strategies i-iii). Hydrophobic and hydrophilic residues were placed appropriately by plotting the C-terminal helical segment in a helical wheel plot (Edmunds diagram). Also we placed the amino acids in such a way to facilitate NMR characterization. Trp, Phe and Leu were chosen as hydrophobic amino acids in $1^{st}$ and $2^{nd}$ generation glycopeptides whereas in $3^{rd}$ generation only Leu was chosen as the hydrophobic residue because it has good helical propensity among the hydrophobic residues.[49] Glu⁻ and Lys⁺ were chosen as hydrophilic residues to form salt-bridges when placed in i and i+4 positions.[47] The presence of residues with side chains that can form hydrogen bonds with the main-chain amide NH or carbonyl groups when located at the beginning (N-cap) or end (C-cap) of α-helices has been found to stabilize and nucleate the helical conformation in peptides and proteins. Asn followed by Asp are the most favored N-cap residues in the natural protein helices forming i, i+2 or i, i+3 type H-bonds with main chain NH hydrogens.[50] Hence, in the $3^{rd}$ generation of helical glycopeptides, Asn was placed immediately following the linker residue to initiate the helix by forming Asx type hydrogen bonding between its side-chain amide with main chain.[51] Other key design features used in the helical segment design were placing the helicogenic Aib residue in the middle and, charged residues Glu and Lys at i and i+4 position to have electrostatic salt bridge in order to increase the stability and solubility, and prevent aggregation.

TABLE 1

Glycopeptides sequences and bioactivity.

| No. | Message-Linker-Helix | δ $IC_{50}$ (nM) | μ $IC_{50}$ (nM) | $A_{50}$ i.c.v. (nmol) | BBB uptake |
|---|---|---|---|---|---|
| 1 | YtGFLGELAS*KWFNALE | | $H_2O$ insoluble | | |
| 2 | YtGFLGELAS*KWFNALES* | 9.5 | 144 | 0.27 | — |
| 3 | YtGFLGELAS*KWFNALES*F | | $H_2O$ insoluble | | |
| 4 | YtGFLGELAS*KWFNALES*FW | | $H_2O$ insoluble | | |
| 5 | YtGFLGALKS*FAES*LS*NA | — | — | — | — |
| 6 | YtGFLGLLKS*FAES*WS*NF | 11.9 | 154 | 0.028 | — |
| 7 | YtGFLGKS*FAELWS*NFLS* | 25.6 | 38.2 | 0.096 | — |
| 8 | YtGFLGLLKS*FWES*WS*NF | — | — | — | — |
| 9 | YtGFLPNLBEKALKS*L | 6.15 | 90.8 | 0.030 | 0.390 |
| 10 | YtGFLβANLBEKALKS*L | 108.9 | 153 | 0.030 | 0.183 |
| 11 | YtGFLGGNLBEKALKS*L | 32.5 | 53 | 0.030 | 0.002 |
| 12 | YtGFLPNLBEKALKS**L | — | — | — | — |

S* = β-O-Glucosyl-L-Serine, S** = β-O-Lactosyl-L-Serine.

Discussion

Glycopeptide 9 has been found to efficiently cross the blood brain barrier in mice, whereas 11 did not, which suggests that the capability of 9 to cross the blood brain barrier is correlated with its high affinity for the lipid bilayer. The binding affinities suggest that the structure of the peptide moiety is responsible for interaction with the membrane. The unglycosylated peptide related to 9 (9u in the Supporting Info) shows slightly reduced binding to the membrane ($K_D$=400 nM, data not shown). Further studies involving the unglycosylated peptides will be necessary to further investigate this point, but it has been observed earlier with shorter glycopeptides that increasing glycosylation also enhanced interactions with liposomes.[11] This could indicate that the carbohydrate is slowing the rate of diffusion from the membrane, perhaps by interacting with the "unstirred layer" of $H_2O$ molecules near the membrane surface.

The available information suggests that the role of the glycoside is simply to "pull" the glycopeptide away from the membrane, allowing the drugs to "hop" from membrane to membrane. These "hops" could be short, keeping the helical backbone conformation, or with helix→random coil transition in the aqueous phase, could be long journeys (FIG. 4). The membrane may be viewed as a catalyst that promotes helix formation[17] (clockwise motion), or alternatively, helix formation in aqueous solution may viewed as an energy barrier that must be surmounted in order to achieve membrane binding (counter-clockwise motion). The CD and NMR results show that the glycopeptides have two distinct behaviors in the presence of, or in the absence of a membrane bilayer. In aqueous media, only nascent helices are observed, with many random coil structures (e.g. FIGS. 4*b*, 1, 2, 3 . . . ) dominating the conformational ensemble. In the presence of a membrane bilayer, a reduced number of amphipathic structures (e.g. A, B, C . . . ) dominate the ensemble. From these and other studies,[10,11,27] it seems clear that the degree of glycosylation (i.e. disaccharide vs monosaccharide) does not have a large effect on the structure of the individual microstates. Thus, the major role of increased glycosylation is the lowering of the energy of the entire aqueous ensemble. Altering the degree of glycosylation should allow for the modulation of aqueous vs membrane-bound state population densities.[52]

While interaction of the amphipathic address segment has obvious implications for receptor binding of the message segment, the implications of the amphipath for drug transport and BBB penetration are very important also. The BBB transport occurs via an absorptive endocytosis process on the blood side of the endothelium of the brain capillaries (FIG. 5), followed by exocytosis on the brain side, leading to an overall transcytotic mechanism. In order for this process to be efficient, the glycopeptide must be able to bind to the membrane for some period of time, and must also be able to exist in the aqueous state for some period of time. Further work needs to be done in order to obtain kinetic information on the glycopeptide-membrane interactions in vitro, as well as further information in vivo on the BBB transport process in order to fully exploit the glycosylation strategy.

Conclusions. CD and NMR studies show that glycopeptides 9-12 form nascent helix-random coil structures in $H_2O$, and that exposure of these aqueous random coils to membrane mimics can produce helical and highly amphipathic secondary structures. Several lines of in vitro research (CD, NMR, PWR) show that membrane-induced helix formation occurs readily in the presence of anionic and zwitterionic membrane mimics. Binding of the helical address region to the membrane can modify agonism at the opioid receptor, and will likely influence the kinetics of opioid binding. Membrane binding affinities (micromolar to nanomolar $K_D$ values) determined by PWR show that membrane affinity rival, or even exceed affinity for the opioid receptor. Amphipathic binding to the membrane also seems to correlate to BBB transport rates. Since there are some 250 known neuropeptides produced in the human brain, a more complete understanding of their glycosylated counterparts could lead to a new vista of pharmacology that exploits the natural binding selectivity of the neuropeptides to treat a wide variety of neurological disorders.

Examples

Experimental Procedures

Materials. Amino acids, coupling reagents and Rink-amide resin were purchased from Advanced ChemTech (Louisville, USA). All other reagents including Sodium dodecyl sulfate-$d_{25}$ used in NMR experiments were purchased from Sigma (St. Louis, Mo.). The deuterated phospholipids, dihexanoyl-sn-glycero-3-phosphatidylcholine-$d_{22}$ (DHPC), 1,2-dimyristoyl-sn-glycero-3-phosphatidylcholine-$d_{54}$ (DMPC) and 1,2-dimyristoyl-sn-glycero-3-phospho-1-glycerol-$d_{54}$ (DMPG) were purchased from Avanti Polar Lipids (Alabaster, Ala.).

Peptide Synthesis and Purification. The required glycosyl amino acids were synthesized using previously published methods.[53] The glycopeptides were synthesized manually by standard solid-phase methods employing fluorenylmethoxycarbonyl (Fmoc) chemistry on rink amide resin.[54] The side chain protecting groups were chosen so as to be removed in a single step at the end of the synthesis while the glycopeptide is still attached to the resin. The side chain protected amino acids used in the synthesis were Fmoc-Lys(Boc)-OH, Fmoc-Glu(OtBu)-OH, Fmoc-Asn(Trt)-OH, Fmoc-DThr(But)-OH and Fmoc-Tyr(But)-OH. The amide couplings were with HBTU/HOBt/DIPEA. Each coupling was performed in a manual peptide synthesis vessel using DMF as solvent by agitating using $N_2$ for 90 minutes. The coupling was monitored by the Kaiser ninhydrin test. Fmoc groups were removed with a solution of 20% piperidine in DMF. Once the glycopeptide was assembled and the final Fmoc group was removed, the -OAc protecting groups were cleaved from the carbohydrate with 80% $H_2NNH_2.H_2O$ in $CH_3OH$. The glycopeptide was cleaved from the resin with a cocktail $F_3CCOOH:Et_3SiH:H_2O:PhOMe:CH_2Cl_2$ (9:0.5:0.5:0.05:1) which also removed the side chain protecting groups. The crude glycopeptides were precipitated with ice-cold ether, filtered, redissolved in $H_2O$ and lyophilized. The glycopeptides were purified by RP-HPLC with a preparative RP(C-18) column using acetonitrile-water gradient containing 0.1% TFA. Homogeneity of the final glycopeptides was assured by analytical RP-HPLC and mass spectrometry.

Circular Dichroism. All of the circular dichroism experiments were carried out on Aviv Associates model 60DS using an Endcal Model RTE4DD water circulator as a temperature-control vehicle. The instrument was calibrated by using d-10-camphorsulphonic acid. The spectra were recorded between 200 and 250 nm by using the continuous mode with a 1.5 nm bandwidth, a three second response and a scan step of 0.5 nm in a cell with a path length of 0.1 cm. Three or five scans were accumulated and averaged for each spectrum. Glycopeptide stock solutions were prepared by weighing the required amount, using Cahn/Ventron Instruments Model 21 automatic analytical electrobalance, to make 1 mL of a 0.5-1.0 mM solution and the pH was adjusted to the desired value. Samples were prepared by diluting the stock solution to 70-80 µM. All observed spectra were baseline-subtracted and smoothed by adjacent average of 5 points using Microcal Origin Ver. 5.0 software (Microcal Software Inc, USA). The molar ellipticities were determined using the formula $[\theta]=[\theta]_{obs} \cdot (MRW)/10 \cdot l \cdot C$, where $[\theta]_{obs}$ observed ellipticity in millidegrees, MRW is the mean residue weight, l is the cell path length in centimeters and C is the glycopeptide concentration in mg/mL. The percent α-helicity was determined by using the formula % helix=$[\theta]_{n \to \pi*}/-40,000$ (1−2.5/n)·100, where n represents the number of amide bonds (including the C-terminal amide) in the glycopeptide and $[\theta]_{n \to \pi**}$ is molar ellipticity of n→π* transition band at 222 nm.[55]

NMR Spectroscopy. All NMR spectra were recorded on a Bruker DRX600 600 MHz spectrometer. Glycopeptide concentration for the NMR experiments varied from 2-3 mM. The glycopeptides were prepared in TFE-water solution by dissolving the peptide in 0.6 ml solution of a premixed 30% TFE-water mixture. The micelle samples were prepared by dissolving the glycopeptide and 100 equivalent of perdeuterated SDS in 0.6 ml of $H_2O/D_2O$ (9:1 ratio by volume). Bicelles were produced from deuterated phospholipids. The zwitterionic bicelles were made by mixing the short chain phospholipid dihexanoyl-sn-glycero-3-phosphatidylcholine-$d_{22}$ (DHPC) and the long chain 1,2-dimyristoyl-sn-glycero-3-phosphatidylcholine-$d_{54}$ (DMPC) in the molar ratio of 2:1 in $H_2O$. The anionic micelles were prepared by substituting 10 mol % of 1,2-dimyristoyl-sn-glycero-3-phospho-1-glycerol-$d_{54}$ (DMPG) for DMPC. The glycopeptide to bicelle ratio was 1:25. After the glycopeptide was added to the bicelle solution, the system was submitted to a series of three freeze/thaw/slight vortex shaking cycles. The pH of the each sample was adjusted to 4.5 by using DCl or NaOD as necessary. TSP (3-(trimethylsilyl)-$d_4$-propionic acid) was added as an internal standard. The experiments in $F_3CCD_2OD/H_2O$ mixtures were at 293 K and for experiments in micelles/bicelles were at 298 or 311 K. Two-dimensional double quantum filtered correlation (DQF-COSY), rotating-frame Overhauser enhancement[56] (ROESY), Nuclear Overhauser enhancement[57] (NOESY), and total correlation spectra[58] (TOCSY) were acquired using standard pulse sequences and processed using XWINNMR (Bruker Inc) and FELIX2000 (Accelrys Inc, San Diego, Calif.), Mixing times for TOCSY spectra were either 80 or 100 ms. Mixing times for ROESY spectra were 150 or 250 ms, and for NOESY spectra were 200 or 300 ms. All experiments were 750 increments in t1, 16/32/64 scans each, 1.5 s relaxation delay, size 2 or 4K, and the spectral processing was with shifted sine bell window multiplications in both dimensions. The water suppression was achieved for $F_3CCD_2OD/H_2O$ samples by pre-saturation of the $H_2O$ signal. Since the $H_2O$ suppression technique did not yield satisfactory results for membrane mimicking solvents, the WATERGATE pulse sequence was used for those solvents to suppress the $H_2O$ signal.[59] Coupling constants ($^3J_{\alpha H-NH}$) were measured from 2D DQF-COSY spectra.

Structure Determination. Distance constraints for the structure calculation were obtained from integral volumes of the ROESY or NOESY peaks. The NOE integral volumes were classified into strong, medium and weak with 3.0, 4.0 and 5.0 Å as upper bound distances, respectively. Molecular dynamics simulation was done with the INSIGHT/DISCOVER package (Accelrys Inc, San Diego, Calif.) with consistent valency force field (CVFF).[60] All the calculations were done in vacuo. A distance-dependent dielectric constant (2.5·R, where R is the distance in Å) was used. Based on the CSI plot of αCH proton and the NOEs pattern observed, the starting structure of all the glycopeptides had extended conformation for the N-terminal segment 1-6, and helical conformation for the C-terminal segment 7-16. The charged form of Glu and Lys side chains were considered throughout the calculations. All peptide bonds were constrained to trans conformation by a 100 kcal mol$^{-1}$ energy penalty. Distance restraints with a force constant of 25 kcal mol$^{-1}$ were applied in the form of a flat-bottom potential well with a common lower bound of 2.0 Å. Only the distance restraints from inter-residue NOEs were included in the calculation. No stereospecific assignments were made and, hence, pseudo atom corrections were applied for all the diastereotopic protons when the NOE restraints were imposed.[61] Dihedral angle restraints based on αCH chemical shift index (CSI) were imposed on the residues displaying helix type deviation. Thus for a CSI of >−0.10 ppm, the φ and ψ restraints were in the range −90° to −30° and −60° to 0°, respectively while for a CSI of ≦−0.10 ppm, the corresponding ranges were −180° to −30° for ψ and −90° to 180° for ψ. The starting structures were minimized with all restraints in place, first with steepest descent algorithm, then by conjugate gradient algorithm, and finally subjected to a simulated annealing protocol. A two hundred picosecond molecular dynamics run was done at 1,000K, followed by cooling to 300K in 7 steps for a total of 35 ps, and then steepest descent and conjugate gradient minimization. One hundred final minimized structures were sampled at 2 picosecond intervals.

Plasmon-waveguide resonance (PWR) spectroscopy. The PWR instrument used for these experiments was Aviv Beta prototype version device obtained from Proterion Corp. (Piscataway, N.J.) having a spectral resolution of 1 millidegree. Self-assembled so lid-supported lipid membranes were prepared according to the method used for the formation of freely suspended lipid bilayers.[62] This involves spreading a small amount of lipid solution across an orifice in a Teflon sheet that separates the thin dielectric film ($SiO_2$) from the aqueous phase. The hydrophilic surface of hydrated $SiO_2$ attracts the polar groups of the lipid molecules, thus inducing an initial orientation of the lipid molecules, with the hydrocarbon chains pointing toward the droplet of excess lipid solution. The next steps of bilayer formation, induced by adding aqueous buffer to the sample compartment of the PWR cell, involve a thinning process and the formation of a plateau-Gibbs border of lipid solution that anchors the membrane to the Teflon spacer. In the present experiments, the lipid films were formed from a solution containing 5 mg/ml egg phosphatidylcholine (PC) in squalene/butanol/methanol (0.05:9.5:0.5, v/v). The lipid was purchased from Avanti Polar Lipids (Birmingham, Ala.). All experiments were carried out at constant temperature of 25° C., using 10 mM Tris buffer containing 0.5 mM EDTA and 10 mM KCl (pH=7.3), in a 1 mL sample cell. Aliquots of the glycosylated peptides, dissolved in deionized water, were injected stepwise in the PWR cell sample and the signal monitored until equilibrium was reached (PWR signal steady). Finally dissociation constants ($K_d$ values) were obtained from plotting the resonance minimum position for the PWR spectra as a function of peptide concentration in the cell sample and fitting using a simple hyperbolic function to describe the binding of a ligand to a lipid bilayer. Data analysis was performed with GraphPad Prism (GraphPad Software Inc., Calif. USA).

First Generation Helical Glycopeptides. In the 1$^{st}$ generation series, the helix length, which comprised the address segment, was varied in order to determine the minimum length required for stable helix formation. An eight-residue amphipathic sequence was used as a base repeating unit for the helix, with the total length used ranging from ten to fourteen residues. (Table 1) The 1$^{st}$ generation glycopeptides were studied by NMR and CD to determine the effect of length on helix stability. The CD data suggested that these glycopeptides were random coil in water and became helical in the presence of SDS micelles. However, no direct correlation could be made between the length of the address helix and the degree of helicity of the glycopeptide on a per-residue basis. In fact, the shortest of the compounds, glycopeptide 1, which had only 12 residues in the address region, displayed the highest level of helicity by CD. Since these glycopeptides were not very soluble in $H_2O$ it was impossible to compare the micelle-bound structures to the aqueous state. NMR studies on the compounds were problematic due to the poor solubility at NMR concentration. Only one of the glycopeptides in the 1$^{st}$ generation, glycopeptide 2, showed significant solubility in water, and was subjected to NMR studies in $H_2O$/$D_2O$ to obtain residue-specific conformational properties. Several helix diagnostic peaks were observed (data not shown). Some of these long-range "helical" NOE's traveled across the glycine spacer residue, which include G3αH⇋L7NH, F4αH⇋L8NH and L5αH⇋A9NH. This suggested that the glycine spacer did not terminate helicity as originally hoped for, and that the conformation of the message segment was affected by the helicity of the address segment. While these, and other NOE's, did suggest some degree of helicity in water, the CD spectrum of glycopeptide 2 in water disputed this conclusion, as the compound was determined to be predominantly random coil by CD.

As glycopeptide 2 was the only water-soluble compound of the 1$^{st}$ generation series, it was the only glycopeptide to be carried on for in vitro binding and in vivo antinociception studies. In both receptor binding assays it was seen that the compound was somewhat δ-selective, with good potency at that receptor. When compared to the previously studied[10] enkephalin-based glycopeptides, activity at the μ-receptor was diminished in both assays, but the drug still possessed enough activity to warrant in vivo experimentation. Upon testing, the $A_{50}$ value of the compound after i.c.v. administration was shown to be 120 pmoles per mouse. This showed that the drug was roughly 18 times more potent than morphine via this route of administration. The $A_{50}$ value provides confirmation of the success of using amphipathic helical C-terminal for BBB penetration, and shows that the α-helical glycopeptide enkephalin analogs can also provide antinociceptive effects in vivo.

TABLE 2

Circular Dichroism Data for 1$^{st}$ and 2$^{nd}$ Generation Glycopeptides.

| Peptide | −[θ]n→π*$^{a,b}$ 222 nm | −[θ]π→π*$^{a,c}$ 205 nm | R$^d$ | % α-helicity$^e$ |
|---|---|---|---|---|
| 1 | 29158 | 28568 | 1.02 | 85 |
| 2 | 23205 | 23451 | 0.99 | 67 |
| 3 | 22719 | 22134 | 1.03 | 65 |
| 4 | 28640 | 29218 | 0.98 | 82 |
| 5 | 20109 | 20776 | 0.97 | 58 |
| 6 | 12628 | 15002 | 0.84 | 37 |
| 7 | 5344 | 11642 | 0.45 | 15 |
| 8 | 13725 | 16043 | 0.86 | 39 |

$^a$The units for [θ] are deg · cm$^2$ · dmol$^{-1}$.
$^b$The negative maxima for the [θ]π→π* was observed between 205 and 209 nm.
$^c$The negative maxima for the [θ]n→π* was observed between 222 and 225 nm.
$^d$R = [θ]$_{n→π*}$/[θ]$_{π→π*}$. A lower value of 0.15-0.40 is observed for 3$_{10}$-helix.
$^e$The % helicity calculated according to the reference 53.
All data was observed in the presence of SDS micelles (30 mM) at pH = 7.0 and 18° C.

Second Generation Helical Glycopeptides. The main concern with this generation was water solubility and the ratio of lipophilicity vs hydrophilicity. All the glycopeptides of this series bore 3 glucosylserines, and were highly water soluble. The conformational properties of these glycopeptides were studied by CD. (FIG. 6 and Table 2) The glycopeptides were largely random coil in water by CD, but they adopt largely helical folding in SDS micelles. This generation of glycopeptides was less helical than the 1$^{st}$ generation. The parameter R, defined as ratio between [θ]n→π*(≅222 nm) and [θ]π→π* (≅205 nm), is 0.45 for glycopeptide 7, which suggests that the glycopeptide backbone might undergo 3$_{10}$-helical folding. It is interesting to note that although the C-terminal helical segment of glycopeptide 7 has the same amino acids as glycopeptide 8, but inverted, they showed distinctly different CD spectra. This result suggests that placing of the amino acids in the peptide sequence is more important than the amino acid properties alone for attaining a specific folding pattern. Attempts to determine three dimensional structures by NMR were hampered by poor quality TOCSY spectra, which was usually essential for unambiguous spin-system identification. The NOESY spectra (but not the ROESY spectra) were of high quality. The probable reason for this is the increased effective molecular weight due to the glycopeptide association with SDS micelles, which is supported by extremely long correlation ($\tau_c$) times.

The i.c.v. administration to mice (results to be published separately) showed that glycopeptides 5, 6 and 7 are potent antinociceptive agents with $A_{50}$ values below 100 pmoles per mouse. There was no direct correlation between the degree of helicity and the level of analgesia that the glycopeptide provided. The least lipophilic and the moderately lipophilic compounds all showed good analgesia with a normal time of efficacy of 2-3 h. This was not the case for the most lipophilic of the series, glycopeptide 8. This compound showed the lowest potency in vivo, but longest duration of action. This was probably directly due to the high lipophilicity of the glycopeptide. This compound would presumably have the highest affinity for a cellular membrane. If the partition coefficient between the surface and the aqueous exterior was high enough, the binding to the surface becomes less of a reversible phenomenon. If this happened, diffusion in the brain was a slower process, meaning the drug did not reach the opioid receptor as quickly. This sluggish diffusion process explains both the lengthened duration, and the lowered potency. The amount of drug that agonized the receptor was never very high in this case, resulting in lower potency. But, because of the high lipophilicity and resulting slow diffusion in the brain, the drug remained available for longer periods of time resulting in longer duration of action.

Third Generation Helical Glycopeptides. The partial success of the earlier generation of the amphipathic helical glycopeptides prompted the redesign of the helix to produce the $3^{rd}$ generation glycopeptides (9-12). The C-terminal amphipathic helical segment was fixed at 9 residues in length to form two complete α-helical turns. In this generation the helix promoting α-aminoisobutyric acid (Aib) residue was placed centrally in the amphipathic helix address segment. When the Aib residue is placed judiciously, shorter peptides as short as eight residues in length have been seen to adopt helical conformation in crystal state as well as in solution state.[63] Some of the $3^{rd}$ generation de novo glycopeptides discussed here showed improved BBB penetration and analgesic effect in mice. Hence, it is interesting to study their molecular conformations, particularly in the presence of membrane model systems in order to shed light on the transport mechanism. Circular dichroism and 2D $^1$H-NMR were our main tools to study the conformation.

Figure 6:
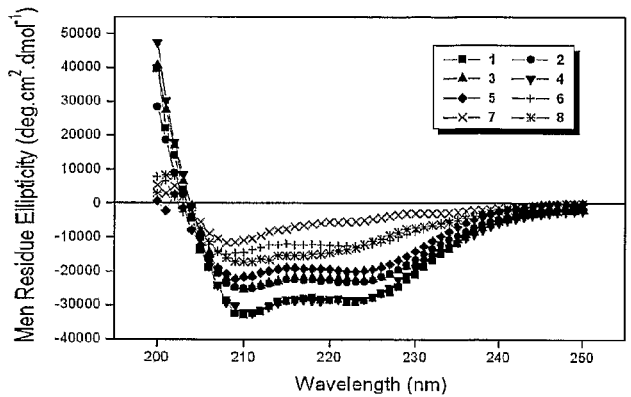
FIG. 6. Far-UV CD spectra of $1^{st}$ and $2^{nd}$ generation helical glycopeptides in SDS amphipathic media. The micelle concentration was 30 mM, pH=7.0, and T=18° C. The Far-UV CD spectra of glycopeptides 9 and 10 in various solvent media. The glycopeptide concentration used was 74-80 μM. The micelle concentration was 30 mM and the bicelle concentration was 10 mM, pH=4.5 at 25° C. Bicelle Z refers to zwitterionic bicelles. Bicelle A refers to anionic bicelles.
Figure 6:
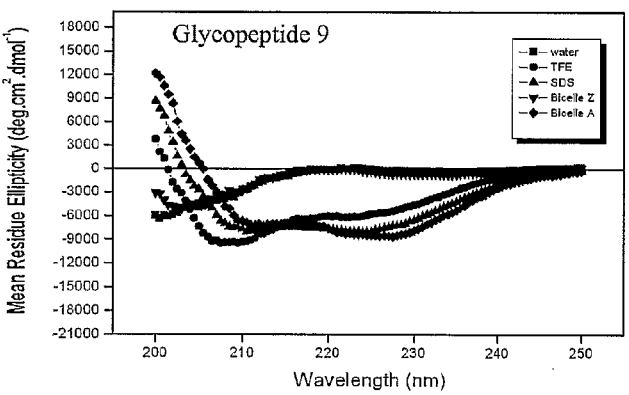
Figure 6:
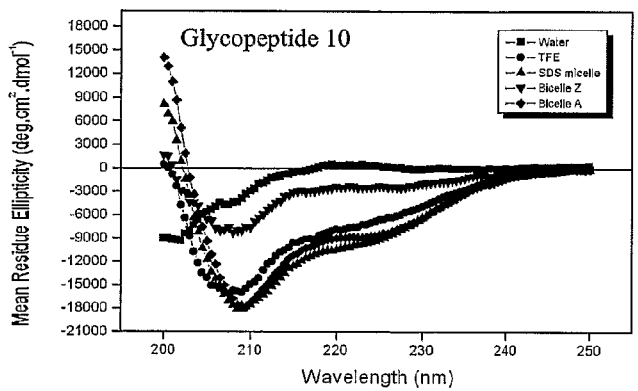

Conformational Analysis by CD. Circular dichroism (CD) is a powerful and simple tool for identifying secondary structure in both peptides and proteins.[64] All the peptides were subjected to CD analysis in $H_2O$, TFE-$H_2O$ mixtures, SDS micelles and phospholipid bicelles. Typical results are shown in FIG. 6. In $H_2O$, a negative band near 200 nm is observed that arises from the π→π* electronic transition and is typical of random coil peptides. It was found that sequences derived from helical regions of proteins often have weak helix CD signals, and can give a series of $d_{NN}$(i, i+1) NOEs, but no long range NOEs. This behavior is explained as nascent helices.[65] In these nascent helices, helix CD signals could be induced by the addition of TFE.[66] All the glycopeptides gave an increased helix CD signal in TFE. The percentage of helicity increases as TFE concentration increases, but reached a maximum at 30% TFE. The increase in helicity in TFE can be attributed to decreased competition by $H_2O$ for hydrogen bonding to the backbone amides. This, taken with the observation of consecutive $d_{NN}$(i, i+1) NOEs, but not long range NOEs in $H_2O$ suggests that the glycopeptides are nascent helices in $H_2O$. In the presence of SDS micelles and anionic bicelles, the band at 200 nm underwent a red shift (higher value) and an additional shoulder appears around 222 nm as a result of the n→π* transition. The appearance of an additional shoulder suggests that the glycopeptides adopt a largely helical conformation that is only present in nascent form (one turn) in $H_2O$. The negative maxima at 222 nm (n→π* transition band) is used to calculate the helical content of polypeptides and proteins. The accepted value for a peptide that is 100% helical is approximately −35,000. It was observed that changes in amplitude of the bands up to 30% depend on length of helix.[67] The amplitude increases as α-helical chain length increases. Therefore, one has to consider the importance of chain-length dependence of the α-helix CD in the quantitative treatment of helix content in proteins and polypeptides. The percentage of helicity is independent of SDS concentration and pH (data not shown). In the presence of zwitterionic bicelles all of the glycopeptides yielded CD spectra similar to that observed in $H_2O$, but anionic bicelles forced them to become more helical. The intensities of the [θ]π→π* band and the [θ]n→π* band are expected to be almost equal for a perfect α-helical peptide. In a $3_{10}$-helix the intensity of the [θ]n→π*(222 nm) band is drastically reduced with respect to [θ]π→π*(205 nm) transition band, and tends to undergo a modest blue shift.[68] This was the case with TFE as the solvent. A modest blue shift and reduced intensity for the [θ]n→π* transition bands are observed for all the glycopeptides in TFE. This suggests that the glycopeptides do not adopt perfect α-helical conformations in TFE solvent. The glycopeptides 9 (Pro/Glc) and 12 (Pro/Lactose), which differ only by the sugar moiety attached, adopt perfect helices in the presence of SDS micelles and in anionic bicelles. The disaccharide increased the percentage of helicity in all the solvents, relative to the monosaccharide. Glycopeptides 10 (β-Ala linker) and 11 (Gly-Gly linker) did not adopt perfect helices in any of the media. It is remarkable to note that a single amino acid mutation at position 6 produced profound changes in the CD spectra. It also suggests that the linker position [i.e. AA(6)] is very important for bioactivity. The glycopeptide 9, which adopted a perfect helix in membrane mimicking media, showed much better BBB penetration rates compared to the other glycopeptides. Thus, it seems clear that the membrane-induced α-helical conformation is critical for its transport activity.

TABLE 3

Circular Dichroism Data for 3rd Generation Glycopeptides.

| Glyco-Peptide | Solvent | $[\theta]n{\to}\pi^{*a,b}$ ≅222 nm | $[\theta]\pi{\to}\pi^{*a,c}$ ≅205 nm | $R^d$ | % α-helicity by CD[e] | % α-helicity by NMR[f] |
|---|---|---|---|---|---|---|
| 9 | H$_2$O | −27 | −4942 | 0.01 | >1 | 20 |
|   | TFE | −6181 | −9445 | 0.60 | 18 | 30 |
|   | SDS | −7063 | −6660 | 1.06 | 24 | 46 |
|   | Bicelle A | −8499 | −4808 | 1.77 | 25 | 44 |
| 10 | H$_2$O | −61 | −6894 | 0.01 | >1 | 17 |
|   | TFE | −7538 | −16203 | 0.47 | 22 | 32 |
|   | SDS | −9892 | −18090 | 0.56 | 29 | 55 |
|   | Bicelle A | −8901 | −17567 | 0.51 | 27 | — |
| 11 | H$_2$O | −61 | −5055 | 0.01 | >1 | 19 |
|   | TFE | −6094 | −11357 | 0.54 | 18 | 28 |
|   | SDS | −5704 | −9796 | 0.58 | 17 | 39 |
|   | Bicelle A | −5646 | −8394 | 0.67 | 17 | — |
| 12 | H$_2$O | −889 | −6962 | 0.13 | >1 | 22 |
|   | TFE | −7753 | −11717 | 0.66 | 23 | 34 |
|   | SDS | −10668 | −9097 | 1.17 | 33 | 29 |
|   | Bicelle A | −11031 | −7960 | 1.39 | 33 | — |

[a]The units for [θ] are deg · cm$^2$ · dmol$^{-1}$.
[b]A minima for [θ]π→π* is observed between 205 and 209 nm.
[c]The negative maxima for the [θ]n→π* is observed between 222 and 225 nm.
[d]R = [θ]$_{n{\to}\pi^*}$/[θ]$_{\pi{\to}\pi^*}$. A lower value of 0.15-0.40 is observed for 3$_{10}$-helix.
[e]The % helicity calculated according to reference 53.
[f]See text for the calculation method.

Figure 7:
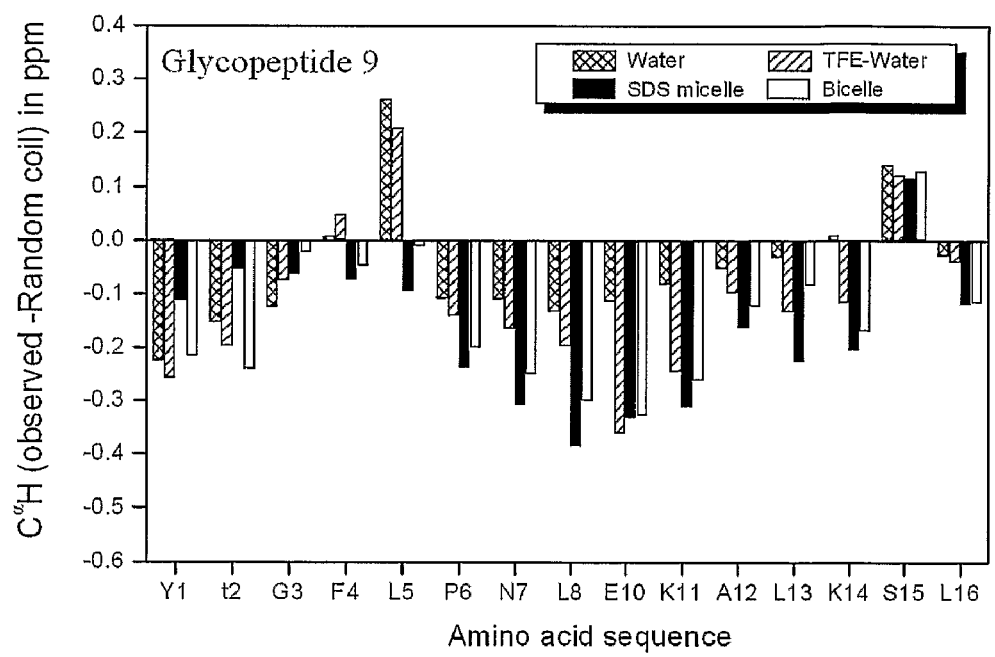
FIG. 7. Plots of chemical shift deviations from random coil values. The Aib and βAla residues are not shown in the plot. Consecutive negative deviations are characteristic of helical conformation. Random coil values were taken from reference 70.
Figure 7:
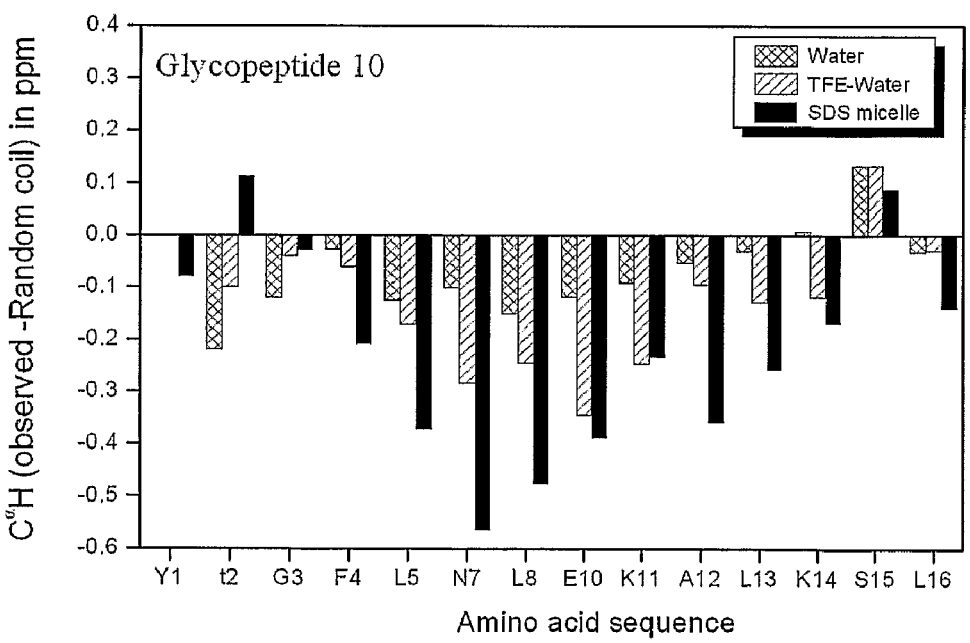

Conformational Analysis by NMR. Circular dichroism provided general information on the overall molecular conformation of glycopeptides in different solvents. To obtain residue-specific information required for better drug design, all the glycopeptides were analyzed using 2D $^1$H-NMR in H$_2$O/D$_2$O, in TFE/H$_2$O/D$_2$O, and in the presence of SDS micelles and phospholipid bicelles. The chemical shift assignments in all media were made by the combined use of TOCSY and NOESY/ROESY spectra. The spin system identification was made using TOCSY spectra, and the sequential assignments were made using TOCSY and ROESY/NOESY. Although some crowding of the off-diagonal cross-peaks was observed, unambiguous proton assignments were made for the glycopeptides in the various solvents based on the observation of sequential d$_{\alpha N}$(i, i+1), d$_{NN}$(i, i+1) and d$_{\beta N}$(i, i+1) NOEs.[69] The complete chemical shift values of the amino acids of all the glycopeptides are provided in the supplementary data. Standard ROESY experiments yielded good quality spectra for samples in H$_2$O and TFE-H$_2$O mixtures, but failed for membrane mimicking solvents. This was due to the association of the glycopeptides with micelles and bicelles, which generated high molecular weight molecular assemblies that increased the correlation times. Standard NOESY experiments were used for SDS and bicelle samples. The association of the glycopeptide amphipaths with micelles and bicelles caused broader NMR signals in all the glycopeptides, however it did not obscure sequential assignments.

αCH Chemical Shift Index. It is now well established that the differences between the observed αCH chemical shifts as compared with random coil values, termed the chemical shift index (CSI), provide a reliable first indication of the specific secondary structure elements present in a (glyco)peptide which is comparable to CD quality.[70] It has even proved to be possible to obtain an estimate of local helix population in (glyco)peptides from the average upfield shift of the αCH proton resonances.[71] The observation of consecutive negative deviations (upfield-shifted αCH resonances) from random coil is indicative of an α-helical conformation. The observed conformational shift values relative to reported random coil values are summarized in FIG. 7. At this point there is no accepted random coil αCH values for glycosylated serine, CSI values for this position are uncertain. The conformational shift values for all solvents were obtained using the random coil values described by Wright and co-workers.[72] Although, these reference shifts were obtained at pH=5.0 at 4.2° C., they appear to be very insensitive to the conditions, as very small deviations (±0.04) were observed when random coil values are obtained at pH=7.0 at 35° C. by Wuthrich and co-workers.[68] The quantification of secondary structure based on αCH chemical shifts is neglected in the literature because various contributions cannot be strictly accounted for, such as electrostatic effects, ring current shifts, and other magnetic anisotropies. However, it is possible to make qualitative comparison of helical content between closely related (glyco) peptides. Since the 3$^{rd}$ generation glycopeptides differ by only one amino acid at position 6, the helical content was obtained based on the αCH chemical shift values (Table 3). The method described by Gierasch and co-workers[69a] was used. First, the average conformational shift was calculated for each glycopeptide by adding all upfield shifts in the helical regions and dividing by the total number of peptide bonds. Then, to obtain the overall helical content for each glycopeptide, the average conformational shift was divided by 0.35 ppm, which was assigned for 100% helicity. Since, there are no random coil values available for β-Alanine and glycosylated serine residues, they were not included in the calculation. The helicogenic Aib residue lacks an α-proton, and there was no correction included in the calculation for the helicity provided by Aib residue. The helical content obtained by this method correlated with the helical content obtained by CD. The helical content was almost the same for all the glycopeptides in water and TFE, but there was a significant difference in the membrane environments. This suggests that each glycopeptide interacts differently with the SDS micelles or phospholipid bicelles. The glycopeptide 11 was shown to have less helical content in the membranes compared to other glycopeptides by both CD and NMR, and was known to exhibit low BBB penetration rates compared to the glycopeptides 9 and 10. Thus, it seems likely that the membrane induced helix plays a major role in transport of the glycopeptides across BBB.

Figure 8:
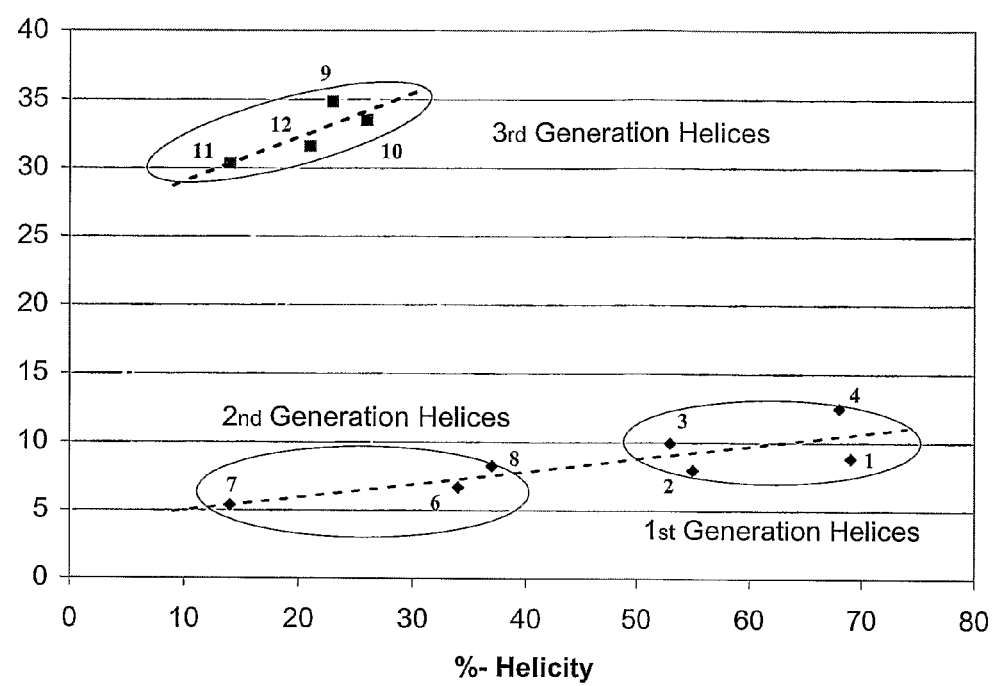
FIG. 8. A plot of RP-HPLC retention times vs percent helicity (per-residue) for the glycopeptides.

Further confirmation of the helical nature of the amphipaths is provided by comparing the reversed phase HPLC retention time (a valid measure of amphipathicity) with the per-residue helicity for each glycopeptide (FIG. 8). This correlation is quite natural because a similar phenomenon is being measured in each case. In one case (y-axis) the equilibrium between an aqueous, random coil (nascent helix) conformational ensemble and a helical micelle-bound amphipathic ensemble is measured in terms of elipticity (CD data). In the other case (x-axis) the equilibrium between the same random coil ensemble and a helical $C_{18}$-silica-bound amphipathic ensemble is being measured in terms of retention time (HPLC data). Two lines are seen because two different solvent systems were used for elution ($CH_3OH/H_2O$ vs $CH_3CN/H_2O$), but the linear correlation is clear in both cases. The helical nature of the peptide moiety is responsible for adsorption to the phase boundary, either the micelle or hydrocarbon modified silica bead, and the degree of helicity determines the degree of adsorption.

Figure 9:
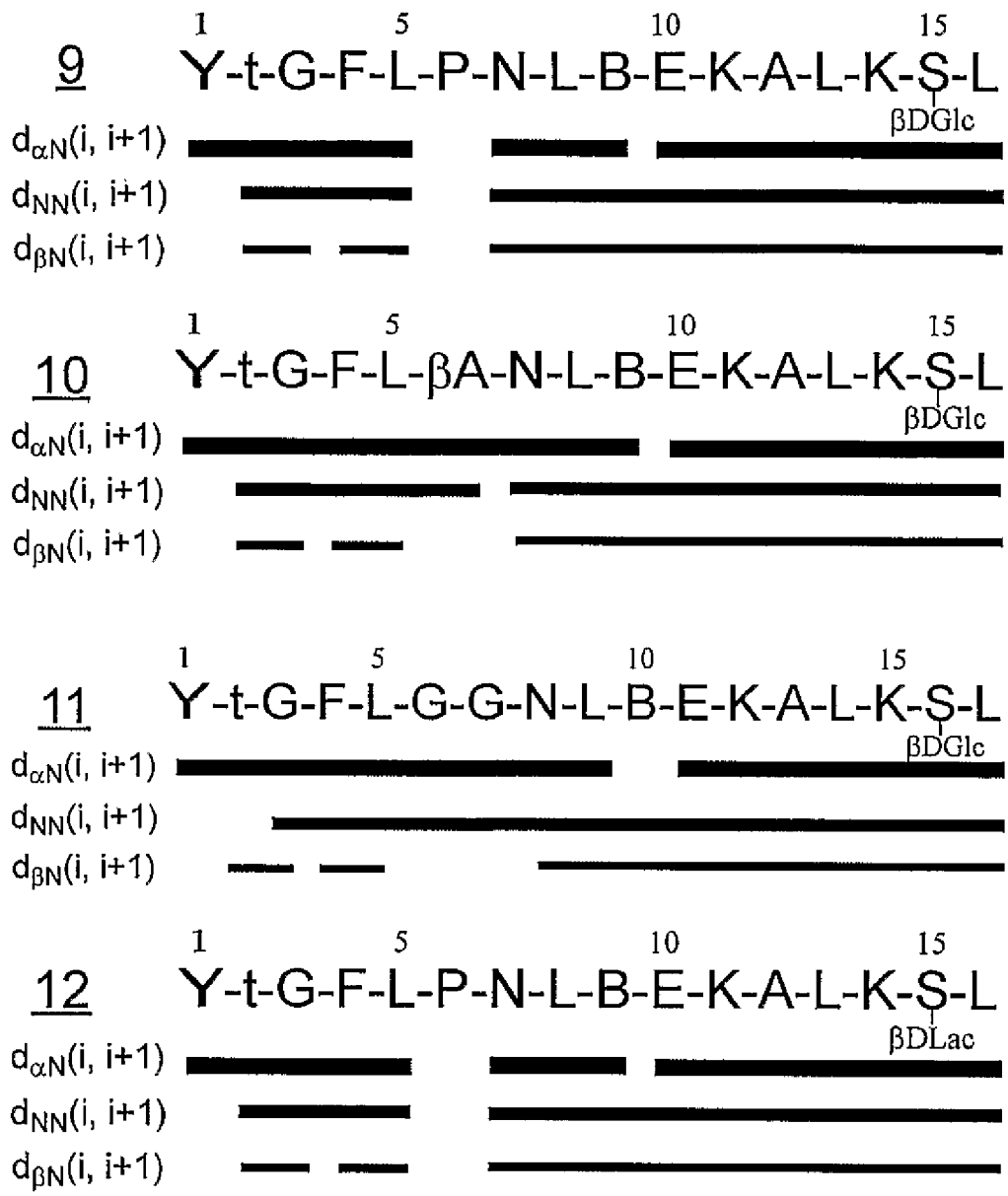
FIG. 9. Summary of ROEs observed in $H_2O:D_2O$ (9:1) at pH=4.5 and 20° C. The line thicknesses indicate the relative ROE intensities.

Conformational Analysis in $H_2O$. The chemical shift of all the glycopeptides are well dispersed in water. The observed ROEs are summarized in FIG. 9. Strong $d_{\alpha N}(i, i+1)$ NOEs, which are generally observed in extended structures, appeared along almost the entire length of the glycopeptides. The $d_{NN}(i, i+1)$ NOEs, which are indicative of local helical or turn conformational states, were observed for all the residues in all the glycopeptides. No other helical signatures for long-range NOEs were observed for any of the glycopeptides. The observation of consecutive $d_{NN}(i, i+1)$ NOEs indicated transient $\alpha_R$ conformational folds for all the residues. These defined only nascent helices, given that no helical signatures medium and/or long range NOEs were observed.[65] The NMR results in water imply that all the glycopeptides, at least the C-terminal segment, have helical propensities, as would be expected from the design considerations.

Figure 10:
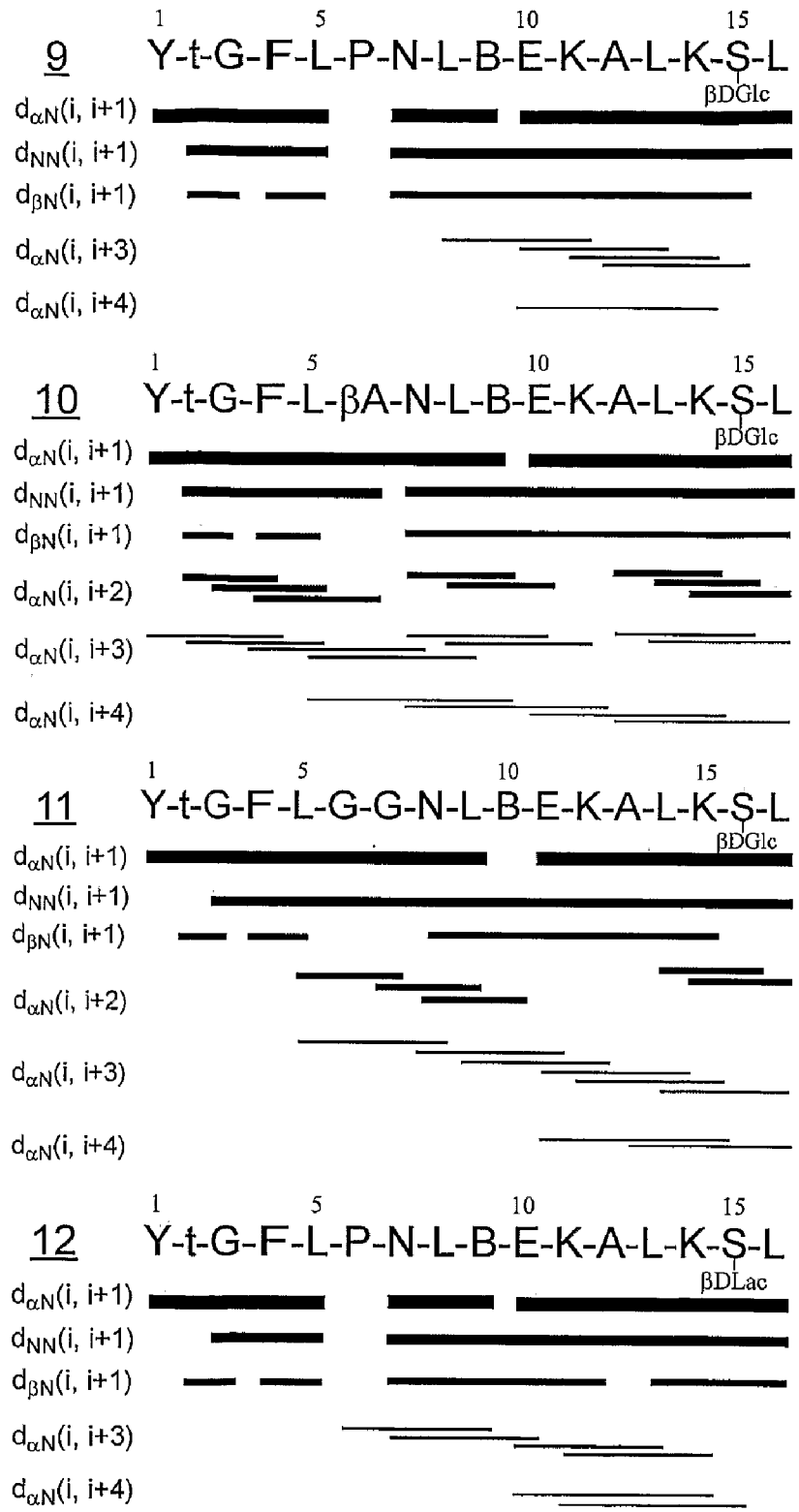
FIG. 10. Summary of ROEs observed in TFE/$H_2O$ (3:7) and pH=4.5 at 15° C. The line thicknesses indicate the approximate ROE intensities.

Conformational Analysis in TFE-$H_2O$. The nascent helices showed additional helical signatures (long range NOEs) in the presence of TFE. The CD experiments showed that the helical content reached a maximum at 30% TFE. Thus, 30% TFE-$H_2O$ (v/v) mixture was chosen for further study. The observed ROEs are summarized in FIG. 10. Many helix-specific NOEs, which include $d_{\alpha N}(i, i+3)$ and $d_{\alpha N}(i, i+4)$, in addition to a continuous stretch of $d_{NN}(i, i+1)$ NOEs, appeared in the C-terminal of all the glycopeptides. The presence of $d_{\alpha N}(i, i+4)$ cross peaks in the C-terminal segment of all the glycopeptides indicated that some population of each glycopeptide adopted an α-helical conformation rather than a $3_{10}$-helical conformation. Since the Aib residue lack a αCH proton, many potential medium and long range NOEs that would otherwise be observed were not seen in the C-terminal. The appearance of $d_{NN}(i, i+1)$ in the segment G(3)-L(5), along with the lack of any medium or long range NOEs in the N-terminal indicated that the glycopeptides might be in local turn conformation, or be in equilibrium between a local helix and an extended conformation. The splitting of Gly αCH protons observed for all the glycopeptides in TFE-$H_2O$ mixture suggested that the Gly(3) of the N-terminal segment exists in a rigid, fixed conformation.

Figure 11:
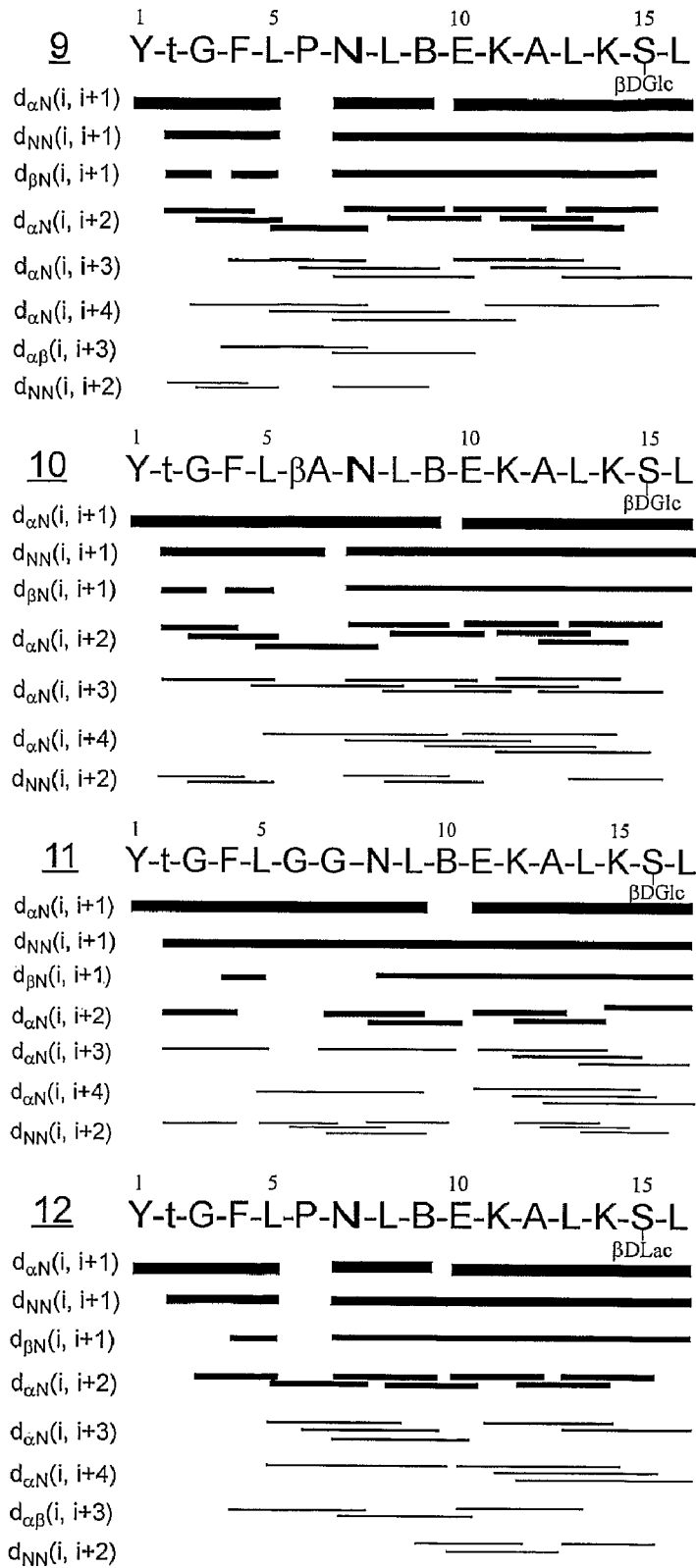
FIG. 11. Summary of NOEs observed in SDS micelle at pH=4.5 and 25° C. The line thicknesses indicate the approximate NOE intensities.

Conformational Analysis in the Presence of SDS Micelles. A glycopeptide/micelle molar ratio of 1:100 was used for all the experiments. In this solvent the line-widths of proton resonances were broad compared to $H_2O$ and TFE-$H_2O$ mixtures, which is due to the association of glycopeptides with SDS micelles—resulting in very high molecular weights. The average SDS micelle is expected to be comprised of about 60-70 detergent molecules,[73] resulting in large aggregates and correspondingly slow molecular tumbling, which leads to excessive broadening of the resonances. However, the spectra were well dispersed with only some crowding, enabling complete sequential assignments to be made. The observed NOEs are summarized in FIG. 11. Evaluation of NOESY spectra of all the glycopeptides revealed features consistent with helical structure. A continuous stretch of sequential $d_{NN}(i, i+1)$ NOEs were observed for almost the entire length of the glycopeptides, along with many helical signatures, e.g. $d_{NN}(i, i+2)$, $d_{\alpha N}(i, i+3)$ and $d_{\alpha N}(i, i+4)$ NOEs. Glycopeptides 9 and 12, which differ only by the sugar moiety attached to Ser(15) residue, showed slightly different NOE patterns. The NOE pattern of the monosaccharide 9, especially the observation of $d_{NN}(i, i+2)[2/4$ and $3/5]$, suggests that the N-terminal message is more ordered than the disaccharide 12.

Simulated annealing molecular dynamics analysis was done for all the glycopeptides to obtain an ensemble of NMR structures using the NOE-derived distance restraints and dihedral angle (φ and ψ) constraints. The C-terminal region Leu(8/9)-Ser(15/16) of all the glycopeptides adopted an α-helical conformation, whereas the N-terminal region was highly flexible in all cases. The opioid message segment was largely random coil (i.e. an equilibrium between local turn conformation and extended conformation) in each case.

Figure 12:
FIG. 12. Summary of NOEs observed in zwitterionic bicelles and pH=4.5 at 25° C. The line thicknesses indicate the approximate NOE intensities.

Conformational Analysis in the Presence of Bicelles. Glycopeptide 9 shows the best BBB penetration among all the helical glycopeptides studied. Hence, it was subjected to further NMR analysis in better membrane mimicking phospholipid bicelle media (FIG. 1). In zwitterionic bicelles glycopeptide 9 displayed the CD spectra characteristic of a random coil conformation, but NMR analysis suggested that the glycopeptide backbone is helical. The CSI plot (FIG. 7) and NOE pattern (FIG. 12) are consistent with the α-helical conformation. The helical signature NOEs $d_{\alpha N}(i, i+3)$ and $d_{\alpha N}(i, i+4)$ were observed throughout the length of the peptide backbone.

Figure 13:
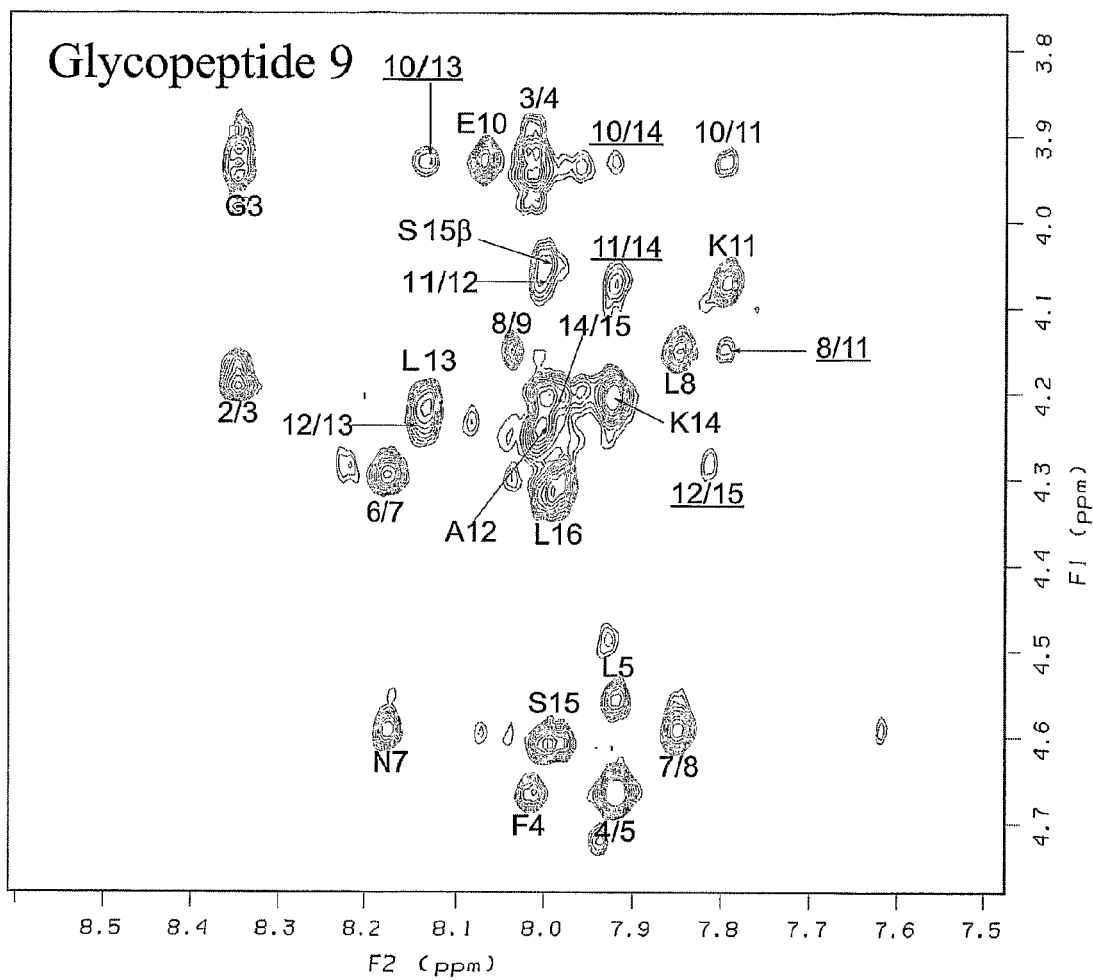
FIG. 13. Fingerprint region (αCH—NH) of the ROESY spectrum in $CF_3CH_2OH:H_2O$ (3:7) and pH=4.5 at 15° C. (mixing time=150 ms). The $d_{\alpha N}(i, i+2)$, $d_{\alpha N}(i, i+3)$ and $d_{\alpha N}(i, i+4)$ ROEs are underlined.
Figure 14:
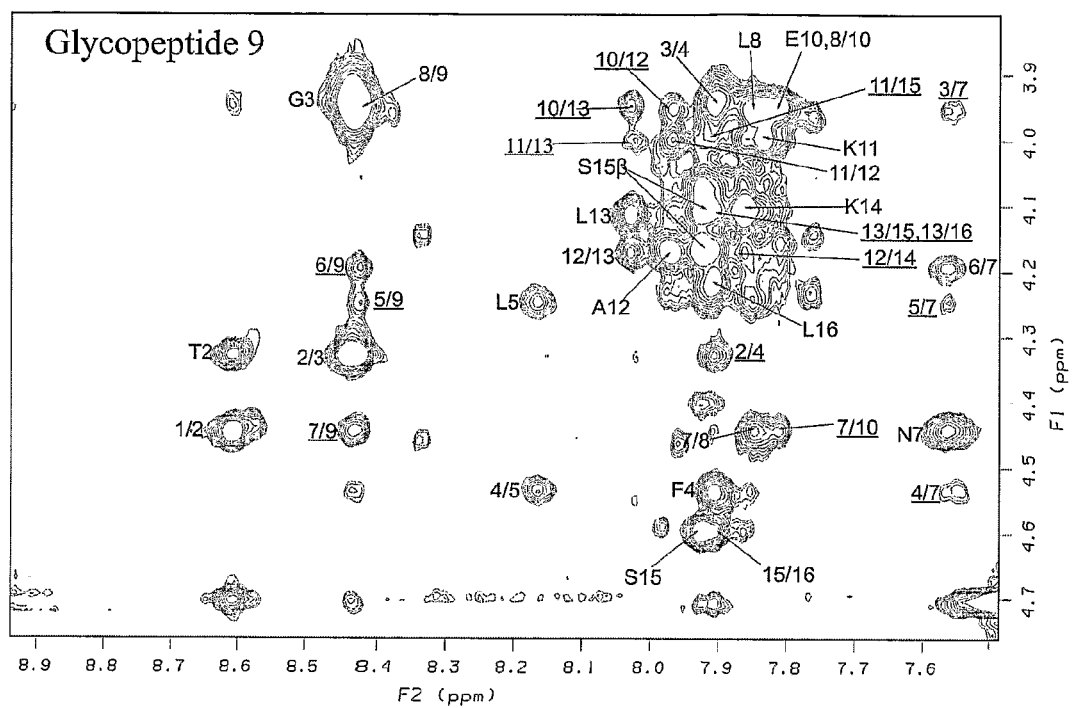
FIG. 14. Fingerprint region of (αCH—NH) of the NOESY spectrum in SDS micelles at pH=4.5 and 25° C. (mixing time=300 msec). The medium and long range NOEs are underlined.
Figure 15:
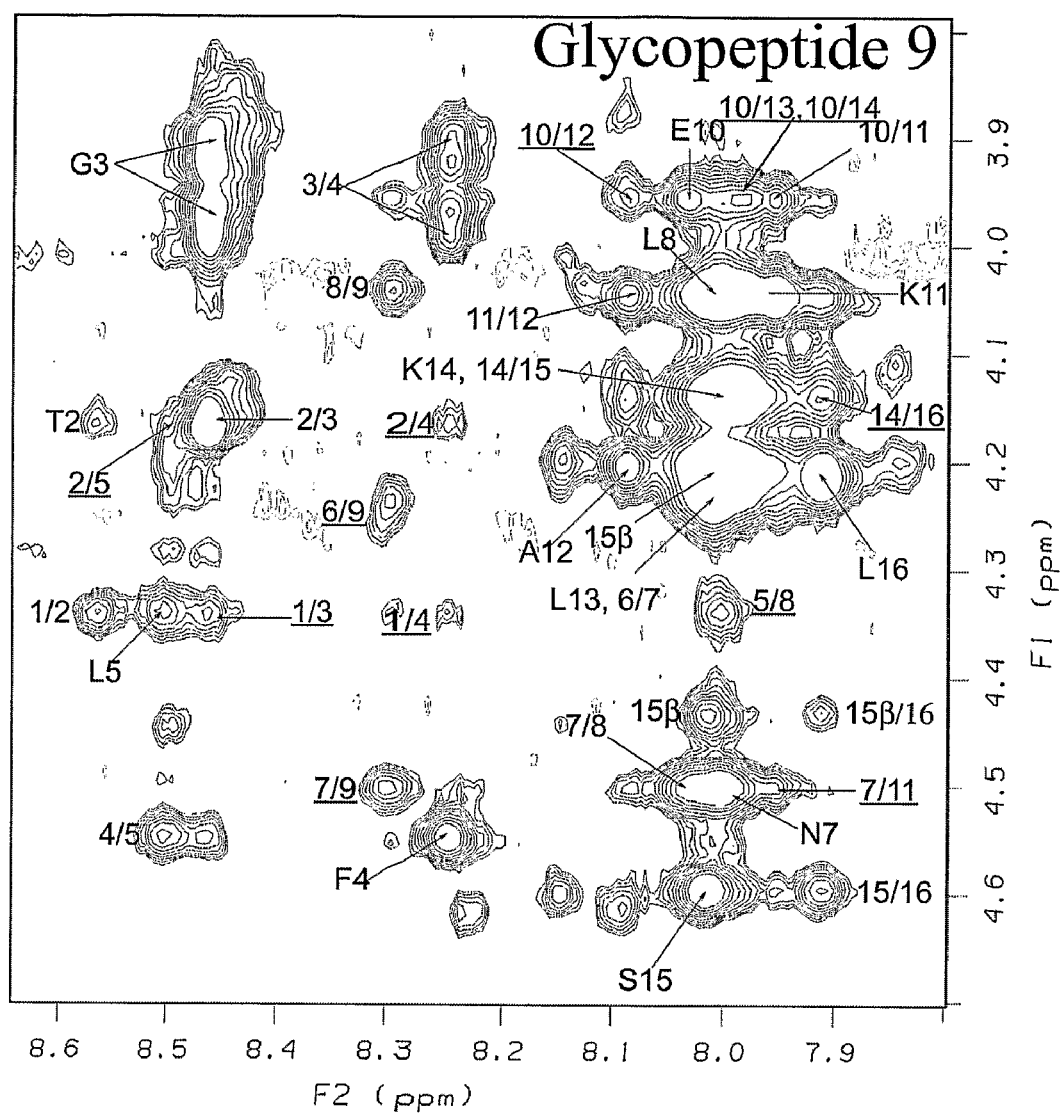
FIG. 15. Fingerprint (αCH—NH) region of the NOESY spectrum in zwitterionic bicelle at pH=4.5 and 25° C. (mixing time=300 msec). The helical signature $d_{\alpha N}(i, i+2)$, $d_{\alpha N}(i, i+3)$ and $d_{\alpha N}(i, i+4)$ NOEs in the fingerprint region are underlined. Observation of sequential $d_{NN}(i, i+1)$ NOEs in the amide region indicates local helical conformation. Some of the potential $d_{NN}(i, i+1)$ NOEs are too near the diagonal to be quantified. The glycopeptide-to-bicelle ratio was 1:25.
Figure 16:
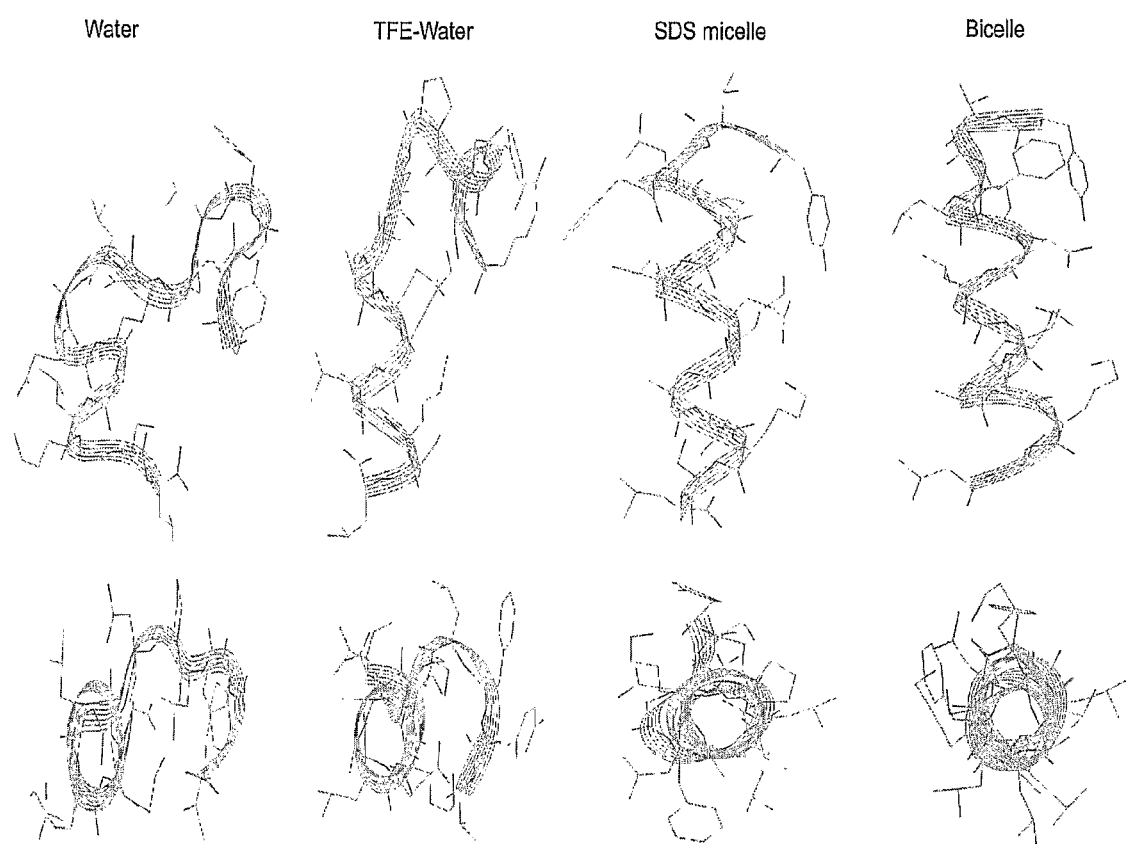
FIG. 16. Comparison of solvent systems on 9. NOE-derived lowest energy conformations resulting from 200 ps simulated annealing molecular dynamics. Helicity increases and the backbone becomes more rigid as the solvent is changed from $H_2O$ to $CF_3CH_2OH/H_2O$ to SDS micelles to bicelles.

It is useful to compare the αCH—NH fingerprint region of the NOSEY/ROESY spectra as the solvent is changed from $CF_3CH_2OH:H_2O$ to micelles to bicelles for glycopeptide 9. Gly(3) is particularly instructive, as we can see it change from an unconstrained environment in TFE:$H_2O$ (FIG. 13), to a somewhat more constrained environment in the presence of micelles (FIG. 14), to a much more constrained environment in the presence of bicelles (FIG. 15) where the αCH protons are distinguishable. A simulated annealing molecular dynamics analysis was done to obtain an ensemble of structures using the NOE-derived distance restraints (FIG. 16). Glycopeptide 9 adopts a continuous helical conformation from residues 5-16, with initiation of the helical conformation at Leu(5) whereas the helix initiation is at Asn(7) in the presence of SDS micelles. The φ torsion angle (N—$C^\alpha$ rotation) of the Pro residue is restricted to $-60°(\pm2°)$, and as a consequence, the local conformations of Pro are largely restricted to $\psi\approx-30°(\pm20°)[\alpha_R]$ or $\psi\approx+120°(\pm30°)$ [polyproline conformation]. When Pro adopts a polyproline conformation [φ=$-60°(\pm20°)$ and $\psi=+120°(\pm30°)$] in a continuous stretch of helix, this results in helix termination.[74] However, Pro in the φ=$-60°(\pm20°)$ and $\psi=+120°(\pm30°)$ conformation is compatible with an α-helical structure. Hence, it is not surprising that 9 forms an extended helix spanning from residues Leu(5)-Ser (15). The observation of $d_{\alpha N}(i, i+3)$ [4/7, 5/8 and 6/9] and $d_{\alpha N}(i, i+4)$ [4/8 and 5/9] indicates that Pro(6) is in the helical stretch.

TABLE 4

Conformational Flexibility of the 3$^{rd}$ Generation Glycopeptides.*

| Residue | Glycopeptide 9 | | Glycopeptide 10 | | Glycopeptide 11 | | Glycopeptide 12 | |
|---|---|---|---|---|---|---|---|---|
| | $\phi$ | $\psi$ | $\phi$ | $\psi$ | $\phi$ | $\psi$ | $\phi$ | $\psi$ |
| N-Terminal Message Segment | | | | | | | | |
| Thr$^2$ | 151(±35) | −94(±9) | −16(±125) | −89(±)14 | 128(±15) | 60(±6) | −107(±23) | −87(±59) |
| Gly$^3$ | 58(±163) | 57(±7) | −62(±126) | −56(±4) | −62(±3) | −20(±5) | −74(±142) | −38(±64) |
| Phe$^4$ | −122(±5) | 19(±4) | −81(±11) | −37(±16) | −88(±4) | −53(±4) | −69(±112) | −40(±44) |
| Leu$^5$ | −81(±3) | −99(±3) | −82(±17) | −9(±40) | −95(±48) | −18(±60) | 47(±56) | −90(±70) |
| C-Terminal Amphipathic Helical Address Segment | | | | | | | | |
| Asn$^{7/8}$ | −148(±1) | −61(±1) | −46(±29) | −1(±13) | −74(±9) | −52(±8) | −129(±7) | −24(±7) |
| Leu$^{8/9}$ | −71(±3) | −26(±2) | −81(±10) | −40(±5) | −63(±5) | −30(±10) | −77(±13) | −31(±4) |
| Aib$^{9/10}$ | −85(±1) | −24(±2) | −58(±2) | −33(±5) | −61(±5) | −54(±4) | −57(±2) | −32(±5) |
| Glu$^{10/11}$ | −91(±2) | −47(±4) | −84(±5) | −50(±6) | −69(±5) | −42(±7) | −76(±10) | −50(±6) |
| Lys$^{11/12}$ | −58(±2) | −30(±4) | −60(±3) | −32(±5) | −63(±3) | −34(±4) | −61(±5) | −29(±6) |
| Ala$^{12/13}$ | −67(±8) | −33(±4) | −75(±7) | −30(±4) | −70(±5) | −31(±4) | −77(±7) | −53(±5) |
| Leu$^{13/14}$ | −73(±6) | −33(±5) | −76(±6) | −52(±4) | −75(±4) | −51(±3) | −66(±3) | −26(±6) |
| Lys$^{14/15}$ | −76(±6) | −32(±5) | −64(±2) | −28(±4) | −64(±2) | −42(±3) | −76(±6) | −32(±6) |
| Ser$^{15/16}$ | −89(±18) | −32(±32) | −81(±11) | −24(±18) | −67(±3) | −27(±4) | −88(±14) | −50(±17) |
| Leu$^{16/17}$ | −85(±6) | −57(±18) | −87(±6) | −58(±7) | 88(±3) | −60(±1) | −112(±19) | −73(±69) |

*The average backbone torsion angles from simulated annealing molecular dynamics calculation using NOE constraints in the presence of SDS micelles. The RMSD values are given in parenthesis. The torsion angles that deviate more than 30° are given in bold letters.

Figure 17:
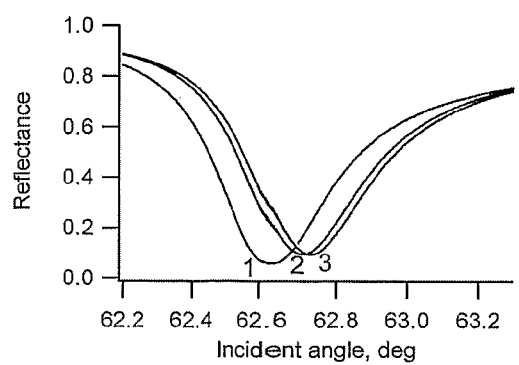
FIG. 17. PWR spectral changes observed for buffer (1), upon lipid bilayer formation (2) and glycopeptide 9 interaction for p- (left panel) and s-polarized (right panel) light. Data shown is for the equilibrated state for 20 nM of each glycopeptide.
Figure 17:
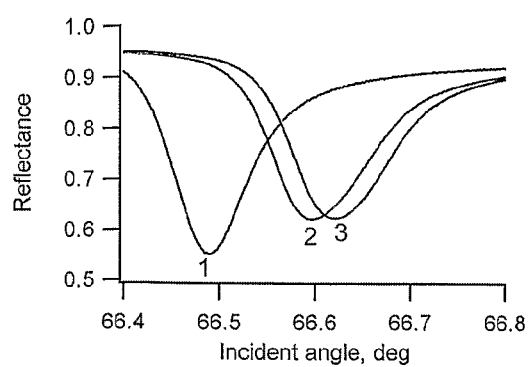
Figure 18:
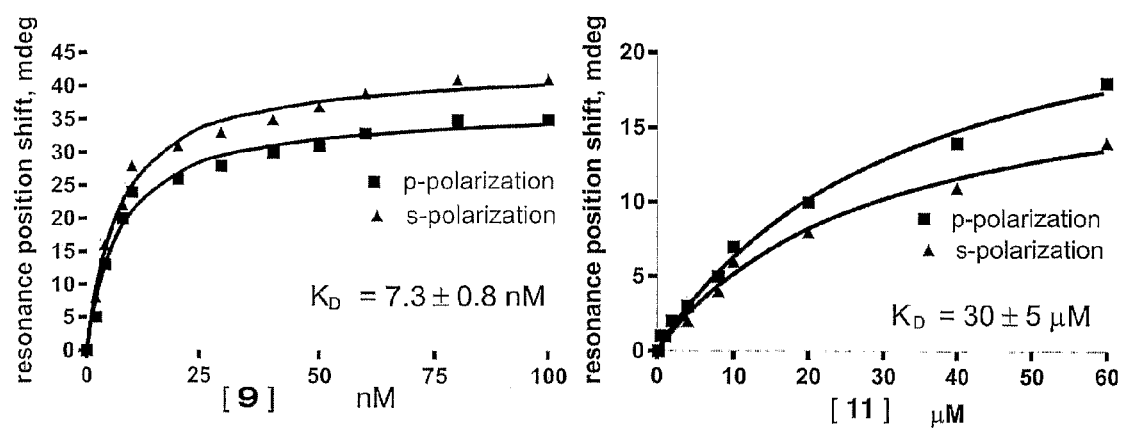
FIG. 18. Binding curves for the interaction of glycopeptides 9 and 11 with the lipid bilayer. The dissociation constant given was calculated by fitting the data through a single hyperbolic function.

Interaction of Glycopeptides with True Lipid Bilayers. Plasmon Waveguide Resonance spectroscopy[75] (PWR) was used to monitor the interaction of two glycopeptides lipid bilayers composed of egg phosphatidyl choline. A solid supported lipid bilayer was made across a small orifice in a Teflon block that is in direct contact with the lipid bilayer[76] and incremental amounts of glycopeptide (dissolved in 10 mM Tris-Cl buffer with 0.5 M EDTA, 10 mM KCl at pH 7.4) were added to the cell sample and spectral changes monitored. PWR results (FIG. 17) shows that lipid bilayer formation and glycopeptide addition cause a shift in the resonance angle position to larger angles for both p- and s-polarized light. In general, such increases in the resonance angle position can be ascribed to an increase in the refractive index as a consequence of the mass increase in the peptide-lipid bilayer.[77] The interaction of the glycopeptide 9 with the lipid bilayer follows a biphasic process, producing an initial shift in the spectra to higher angles (data not shown) followed by a small shift to smaller angles (still positive relative to the bilayer) occurring on the order of minutes (curve 3). The shifts in the resonance angle can be plotted for the incremental additions of each glycopeptide to the lipid bilayer, and fitted through a hyperbolic fit to provide affinity constants. One can see in FIG. 18 that the glycopeptide 9 has a very high affinity for the lipid bilayer (7-8 nM). It is interesting to note that the interaction of the glycopeptide 9 with the lipid bilayer produces larger shifts in s- than in p-polarization, so larger structural changes are occurring in the lipid/peptide in the parallel plane to the lipid bilayer than the perpendicular plane.[78] This data, together with the fact that this glycopeptide is amphipathic and α-helical, shows that the glycopeptide is interacting with the lipid bilayer with its longer axis oriented parallel to the lipid bilayer. This is consistent with both the NMR data, as well as the principles used to design the amphipathic address region. The interaction of glycopeptide 11 with the lipid bilayer is about 4,000 times weaker ($K_D$=30 μM), with much smaller spectral shifts observed, even at μM concentration of the glycopeptide. The spectral changes, contrary to what was observed with 9, follow a slower, monotonic process (data not shown).

TABLE 5

The Average Backbone Torsion Angles of Glycopeptide 9 in Bicelle Media.*

| Residue | $\phi$ | $\psi$ | Conformation |
|---|---|---|---|
| Thr$^2$ | 62(±9) | 61(±3) | Random coil |
| Gly$^3$ | −4(±2) | 62(±1) | Random coil |
| Phe$^4$ | −162(±6) | −52(±9) | Random coil |
| Leu$^5$ | −54(±5) | −55(±7) | α-helix |
| Pro$^6$ | −61(±5) | −40(±7) | α-helix |
| Asn$^7$ | −71(±3) | −46(±5) | α-helix |
| Leu$^8$ | −63(±3) | −34(±4) | α-helix |
| Aib$^9$ | −58(±3) | −37(±3) | α-helix |
| Glu$^{10}$ | −82(±6) | −44(±9) | α-helix |
| Lys$^{11}$ | −63(±3) | −34(±4) | α-helix |
| Ala$^{12}$ | −73(±4) | −33(±3) | α-helix |
| Leu$^{13}$ | −72(±3) | −36(±3) | α-helix |
| Lys$^{14}$ | −73(±3) | −30(±3) | α-helix |
| Ser$^{15}$ | −79(±8) | −23(±14) | α-helix |
| Leu$^{16}$ | −89(±4) | −59(±6) | α-helix |

*From simulated annealing molecular dynamics calculation using NOEs measured in the presence of zwiterionic bicelles. The RMSD values are given in parenthesis.

Obviously, numerous modifications and variations of the present invention are possible in light of the above teachings. It is therefore to be understood that within the scope of the appended claims, the invention may be practiced otherwise than as specifically described herein.

REFERENCES

1. McNally, G. P.; Akil, H. Opioid peptides and their receptors: overview and function in pain modulation. In *Neuropsychopharmacology: the Fifth Generation of Progress*, Davis, K. L.; Charney, D.; Coyle, J. T.; Nemeroff, C. Eds, Lippincott Williams & Wilkins, Philadelphia, 2002, Chapter 3, pp. 35-46.
2. Adessi, C.; Soto, C. *Cur. Med. Chem.* 2002, 9, 963-978.
3. Reese, T. S.; Karnovsky, M. J. *J. Cell. Biol.* 1967, 34, 207-217.
4. Pardridge, W. M. *Introduction to the Blood-Brain Barrier*, Cambridge University Press: New York, 1993.

5. Breig, N. H.; Fredericks, W. R.; Holoway, H. W.; Soncrant, T. T.; Rapoport, S. I. *J. Pharmacol. Exp. Ther.* 1988, 245, 581-586.
6. a) Hruby, V. J.; Mosberg, H. I. *Peptides* 1982, 3, 329-336. b) Mosberg, H. I., Hurst, R., Hruby, V. J.; Galligan, J. J.; Burks, T. F.; Gee, K.; Yamamura, H. I. *Biochem. Biophys. Res. Commun.* 1982, 106, 506-512.
7. Hruby, V. J. *Biopolymers* 1993, 33, 1073-1082.
8. a) Bodor, N.; Prokai, L.; Wu, W. M.; Farag, H.; Jonalagadda, S.; Kawamura, M.; Simpkins, J. *Science* 1992, 257, 1698-1700. b) Rousselle, C.; Clair, P.; Lefauconnier, J. M.; Kaczorek, M.; Scherrmann, J. M.; Temsamani, *J. Mol. Pharmacol.* 2000, 57, 679-686.
9. a) Albert, R.; Marbach, P.; Bauer, W.; Briner, U.; Fricker, G.; Bruns, C.; Pless, J. *Life Sci.* 1993, 53, 517-525. b) Polt, R.; Porreca, F.; Szabo, L. Z.; Bilsky, E. J.; Davis, P.; Abbruscato, T. J.; Davis, T. P.; Harvath, R.; Yamamura, H. I.; Hruby, V. J. *Proc. Natl. Acad. Sci. USA* 1994, 91, 7114-7118. c) Negri, L.; Lattanzi, R.; Tabacco, F.; Orru, L.; Severini, C.; Scolaro, B.; Rocchi, R. *J. Med. Chem.* 1999, 42, 400-404. d) Tomatis, R.; Marastoni, M.; Balboni, G.; Guerrini, R.; Capasso, A.; Sorrentino, L.; Santagada, V.; Caliendo, G.; Lazarus, L. H.; Salvadori, S. *J. Med. Chem.* 1997, 40, 2948-52.
10. a) Egleton, R. D.; Mitchell, S. A.; Huber, J. D.; Palian, M. M.; Polt, R.; Davis, T. P. *J. Pharmacol. Exp. Ther.* 2001, 299, 967-972. b) Bilsky, E. J.; Egleton, R. D.; Mitchell, S. A.; Palian, M. M.; Davis, P. Huber, J. D.; Jones, H.; Yamamura, H. I.; Janders, J.; Davis, T. P.; Porreca, F.; Hruby, V. J.; Polt. R. *J. Med. Chem.* 2000, 43, 2586-2590. c) Elmagbari, N. O.; Egleton, R. D.; Palian, M. M.; Lowery, J. J.; Schmid, W. R.; Davis, P.; Navratilova, E.; Dhanasekaran, M.; Keyari, C. M.; Yamamura, H. I.; Porreca, F.; Hruby, V. J.; Polt, R.; Bilsky, E. J. *J. Pharmacol. Expt. Ther.* 2004, 311, 290-297.
11. Palian, M. M.; Boguslavsky, V. I.; O'Brien, D. F.; Polt, R. *J. Am. Chem. Soc.* 2003, 125, 5823-5831.
12. a) Susaki, H.; Suzuki, K.; Yamada, H.; Okuno, S.; Watanabe, H. K. *Biol. Pharm. Bull.* 1999, 22, 1094-1098. b) Suzuki, K.; Susaki, H.; Okuno, S.; Sugiyama, Y. *J. Pharmacol. Exp. Ther.* 1999, 288, 57-64. c) Suzuki, K., Susaki, H.; Okuno, S.; Yamada, H.; Watanabe, H. K.; Sugiyama, Y. *J. Pharmacol. Exp. Ther.* 1999, 288, 888-897.
13. Egleton, R. D.; Mitchell, S. A.; Huber, J. D.; Janders, J.; Stropova, D.; Polt, R.; Yamamura, H. I.; Hruby, V. J.; Davis, T. P. *Brain Res.* 2000, 881, 37-46.
14. a) Gysin, B.; Schwyzer, R. *Arch. Biochem. Biophys.* 1983, 225, 467-474.
15. Lee, N. M.; Smith, A. P. *Life Sci.* 1980, 26, 1459.
16. Graf, L.; Cseh, C.; Barat, E.; Ronai, A. Z; Szekely, J.; Kennesey, A.; Bajusz, S. *Ann. N.Y. Acad. Sci.* 1977, 297, 63.
17. Schwyzer, R. *Biochemistry* 1986, 25, 6336-6342.
18. Taylor, J. W.; Osterman, D. G.; Miller, R. J.; Kaiser, E. T. *J. Am. Chem. Soc.,* 1981, 103, 6965-6966.
19. a) Taylor, J. W.; Kaiser, E. T.; *Int. J. Pept. Protein Res.* 1989, 34, 75-80. b) Blanc, J. P.; Taylor, J. W.; Miller, R. J.; Kaiser, E. T. *J. Biol. Chem.* 1983, 258, 8277-8284. c) Taylor, J. W.; Miller, R. J.; Kaiser, E. T. *J. Biol. Chem.* 1983, 258, 4464-4471.
20. a) Taylor, J. W.; Miller, R. J.; Kaiser, E. T. *Mol. Pharmacol.* 1982, 22, 657-666. b) Taylor, J. W.; Kaiser, E. T. *Methods Enzymol.* 1987, 154, 473-499.
21. Goldstein, A.; Fischli, W.; Lowney, L. I.; Hunkapiller, M.; Hood, L. *Proc. Natl. Acad. Sci. USA.* 1981, 78, 7219-7223.
22. Chavkin, C.; Goldstein, A. *Proc. Natl. Acad. Sci. USA.* 1981, 78, 6543-6547.
23. a) Renugopalakrishnan, V.; Rapaka, R. S.; Huang, S.-G.; Moore, S.; Houston, T. B. *Biochem. Biophys. Res. Commun.* 1988, 151, 1220-1225. b) Zhou, N.; Gibbons, W. A. *J. Chem. Soc., Perkin Trans.* 1986, 2, 637-644. c) Maroun, R.; Mattice, W. L. *Biochem. Biophys. Res. Commun.* 1981, 103, 442-446. d) Spadaccini, R.; Crescenzi, O.; Picone, D.; Tancredi, T.; Temussi, A. *J. Peptide Sci.* 1999, 5, 306-312.
24. Tessmer, M.; Kallick, D. A. *Biochemistry* 1997, 36, 1971-1981.
25. a) Luna, F-D. T.; Collins, N.; Stropova, D.; Davis, P.; Yamamura, H. I.; Porreca, F.; Hruby, V. J. *J. Med. Chem.* 1996, 39, 1136-1141.
26. Zhang, C.; Miller, W.; Valenzano, K. J.; Kyle, D. J. *J. Med. Chem.* 2002, 45, 5280-5286.
27. Egleton, R. D.; Bilsky, E. J.; Tollin, G.; Dhanasekaran, M.; Lowery, J.; Alves, I.; Davis, P.; Porreca, F.; Yamamura, H. I.; Yeomans, L.; Keyari, C. M.; Polt, R. *Tetrahedron Asym.* 2005, 16, 65-75)
28. Buck, M. Quart. *Reviews Biophys.* 1998, 31, 297-355.
29. a) Henry, G. D.; Sykes, B. D. *Methods Enzymol.* 1994, 239, 515-535. b) Damberg, P.; Jarvet, J.; Gräslund, A. *Methods Enzymol.* 2001, 339, 271-285.
30. a) Vold, R.; Prosser, R. S. *J. Mag. Reson.* 1996, 113, 267-271. b) Struppe, J.; Whiles, J. A.; Vold, R. R. *Biophys. J.* 2000, 78, 281-289. c) Struppe, J.; Komives, E. A.; Taylor, S. S.; Vold, R. R. *Biochemistry* 1998, 37, 15523-15527.
31. a) Luchette. P. A.; Vetman, T. N.; Prosser, R. S.; Hancock, R. E. W.; Nieh, M. P.; Glinka, C. J.; Krueger, S.; Katsaras, J. *Biochimica. Biophysica. Acta.* 2001, 1513, 83-94. b) Glover, K. J.; Whiles, J. A.; Wu, G.; Yu, J.; Deems, R.; Struppe, J. O.; Strark, R. E., Komives, E. A.; Vold, R. R. *Biophys. J.* 2001, 81, 2163-2171.
32. Sanders, C. R.; Landis, G. C. *Biochemistry* 1995, 34, 4030-4040.
33. a) Marcotte, I.; Separovic, F.; Auger, M.; Gagné, S. M. *Biophys. J.* 2004, 86, 1587-1600. b) Chatterjee, C.; Mukhopadhyay, C. *Biopolymers* 2003, 70, 512-521.
34. a) Bárány-Wallje, E.; Andersson, A.; Gräslund, A.; Mäler, L. *FEBS Lett.* 2004, 567, 265-269. b) Lindberg, M.; Biverståhl, H.; Gräslund, A.; Mäler, L. *Eur. J. Biochem.* 2003, 270, 3055-3063.
35. Adam, G.; Delbruck, M. In Structural chemistry and molecular biology, pp 198-ff, Rich, R.; Davidson, N., Eds., Freeman & Co., San Francisco (1968).
36. Pauling, L.; Corey, R. B.; Branson, H. R. *Proc. Natl. Acad. Sci. USA.* 1951, 37, 205-211. b) Perutz, M. F. New X-Ray Evidence on the Configuration of Polypeptide Chains. *Nature* 1951 167, 1053. c) Chothia, C.; *Annu. Rev. Biochem.* 1984, 53, 537-572.
37. Segrest, J. P.; Jackson, R. L.; Morrisett, J. D.; Gotto, A. M., Jr. *FEBS Lett.* 1974, 38, 247-253.
38. a) Cornette, J. L.; Cease, K. B.; Margalit, H.; Spouge, J. L.; Berzofsky, J. A; DeLisi, C. *J. Mol. Biol.* 1987, 195, 659-685. b) Epand, R. M.; Shai, Y.; Segrest, J. P.; Anantharamaiah, G. M.; *Biopolymers* 1995, 37, 319-338.
39. Segrest, J. P.; Loof, H. D.; Dohlman, J. G.; Brouillette, C. G.; Anantharamaiah, G. M. *Proteins: Struct., Funct., Genet.* 1990, 8, 103-117.
40. Fernandez-Carneado, J., Kogan, M. J., Pujals, S., Giralt, E. Amphipathic peptides and drug delivery. *Biopolymers (Peptide Science)* 2004, 76, 196-203.
41. (a) Lin, J. C.; Barua, B.; Andersen, N. H. *J. Am. Chem. Soc.* 2004, 126, 13679-13684. (b) Lifson, S.; Roig, A. *J. Chem. Phys.* 1961, 34, 1963-1974. (b) Doig, A. J.; Chakrabartty, A.; Klingler, T. M.; Baldwin, R. L. *Biochemistry* 1994, 33, 3396-3403.

42. Zajac, J.-M.; Gacel, G.; Petit, F.; Dodey, P.; Rosignol, P.; Roques, B. P. *Biochem. Biophys. Res. Commun.* 1983, 111, 390-397.
43. Chakrabarthy, A.; Baldwin, R. L. *Adv. Protein Chem.* 1995, 46, 141-176.
44. Marqusee, S.; Robbins, R. L.; Baldwin, R. L. *Proc. Natl. Acad. Sci. USA* 1989, 86, 5286-5290.
45. Karle, I. L.; Balaram, P. *Biochemistry* 1990, 29, 6747-6756.
46. Marqusee, S.; Baldwin, R. L. *Proc. Natl. Acad Sci. USA,* 1987, 84, 8898-8902.
47. Bracken, C.; Gulyas, J.; Taylor, J. W.; Baum, J. *J. Am. Chem. Soc.* 1994, 116, 6431.
48. Schneider, J. P; Kelly, J. W. *Chem. Rev.* 1995, 95, 2169-2187.
49. Lyu, P. C.; Liff, M. I.; Marky, L. A.; Kallenbach, N. R. *Science* 1990, 250, 669-673. b) O'Neil, K. T.; DeGrado, W. F. *Science* 1990, 250, 646-651. c) Padmanabhan, S.; Marqusee, S.; Ridgeway, T.; Laue, T. M.; Baldwin, R. L. *Nature* 1990, 344, 268-270.
50. (a) Presta, L. G.; Rose, G. D. *Science* 1988, 240, 1632-1641. (b) Richardson, J. S.; Richardson, D. C., Amino acid preferences for specific locations at the ends of α-helices. *Science* 1988, 240, 1648-1652. (c) Aurora, R.; Rose, G. D. *Protein Sci.* 1995, 4, 1325-1336.
51. Abbbadi, A.; Mcharfi, M.; Aubry, A.; Premilat, S.; Boussard, G.; Marraud, M. *J. Am. Chem. Soc.* 1991, 113, 2729-2735.
52. This notion of two states has been referred to as biousian. See reference 27 for more details.
53. Mitchell, S. A.; Pratt, M. R.; Hruby, V. J.; Polt, R. *J. Org. Chem.* 2001, 66, 2327-2342.
54. Chan, W. C.; White, P. D. In *Fmoc Solid phase peptide synthesis: A practical approach*; Chan, W. C.; White, P. D., Eds.; Oxford, 2000; pp 41-76.
55. Scholtz, J. M.; Marqusee, S.; Baldwin, R. L.; York, E. J.; Stewart, J. M.; Santoro, M.; Bolen, D. W. *Proc. Natl. Acad. Sci. U.S.A.* 1991, 88, 2854-2858.
56. Rance, M. *J. Magn. Reson.* 1987, 74, 557-564.
57. Kumar, A.; Ernst, R. R.; Wuthrich, K., *Biochem. Biophys. Res. Commun.* 1985, 63, 207-213.
58. Davis, D. G.; Bax, A., *J. Am. Chem. Soc.* 1985, 107, 2821-2823.
59. Piotto, M.; Daudek, V.; Sklenar, V., *J. Biomol. NMR.* 1992, 2, 661-665.
60. a) Hagler, A. T.; Lifson, S.; Dauber, P. *J. Am. Cher. Soc.* 1979, 101, 5122-5130. b) Dauber-Osguthorpe, P.; Roberts, V. A.; Osguthorpe, D. J.; Wolff, J.; Genest, M.; Hagler, A. T. *Proteins: Structure, Function and Genetics* 1988, 4, 31-47.
61. Wuthrich, K.; Billeter, M.; Braun, W. *J. Mol. Biol.* 1983, 169, 949-961.
62. Mueller, P.; Rudin, D. O.; Tien, H. T.; Wescott, W. C. *Nature* 1962, 194, 979-980.
63. a) Aravinda, S.; Shamala, N.; Roy, R. S.; Balaram, P. *Proc. Indian Acad. Sci. (Chem. Sci.)* 2003, 115, 373-400. b) Dhanasekaran, M.; Fabiola, F.; Pattabhi, V.; Durani, S. *J. Am. Chem. Soc.* 1999, 121, 5575-5576.
64. Woody, R. W. *Methods Enzymol.* 1995, 246, 34-71.
65. a) Dyson, H. J.; Rance, M.; Houghten, R. A.; Wright, P. E.; Lerner, R. A. *J. Mol. Biol.* 1988, 201, 201-217. b) Werner, J. H.; Dyer, R. B.; Fesinmeyer, R. M.; Andersen, N. H. *J. Phys. Chem. B* 2002, 106, 487-494.
66. a) Millhauser, G. L. *Biochemistry* 1995, 34, 3873-3877. b) Andersen, N. H.; Liu, Z. H.; Prickett, K. S. *FEBS Lett.* 1996, 399, 47-52.
67. a) Applequist, J. *J. Chem. Phys.* 1979, 71, 4332-4338. b) Manning, M. C.; Woody, R. W. *Biopolymers* 1991, 31, 569-586.
68. a) Toniolo, C.; Polese, A.; Fornaggio, F.; Crisma, M.; Kamphuis, J. *J. Am. Chem. Soc.* 1996, 118, 2744-2745. b) Toniolo, C.; Formaggio, F.; Tognon, S.; Broxterman, Q. B.; Huang, R.; Setnicka, V.; Keiderling, T. A.; McColl, I. H.; Hecht, L.; Barron, L. D. *Biopolymers* 2004, 75, 32-45
69. Wuthrich, K. *NMR of proteins and nucleic acids*; Wiley: New York, 1986.
70. Wishart, D. S.; Sykes, B. D. *Methods Enzymol.* 1994, 239, 363-393.
71. a) Rizo, J.; Blanco, F. J.; Kobe, B.; Bruch, M. D.; Oierasch, L. M. *Biochemistry* 1993, 32, 4881-4894. b) Merutka, G.; Morikis, D.; Brüschweiler, R.; Wright, P. E. *Biochemistry* 1993, 32, 13089-13097.
72. Merutka, G.; Dyson, H. J.; Wright, P. E. *J. Biomol. NMR.* 1995, 5, 14-24.
73. Helenius, A.; McCaslin, D. R.; Fries, E.; Tanford, C. *Methods Enzymol.* 1979, 56, 734-749.
74. Gunasekaran, K.; Nagarajaram, H. A.; Ramakrishman, C.; Balaram, P. *J. Mol. Biol.* 1998, 275, 917-932.
75. Plasmon waveguide resonance (PWR) is slightly different from surface plasmon resonance (SPR) in that one can obtain information both in the s-mode (parallel to the membrane surface) and the p-mode (perpendicular to the membrane surface). Schuck, P. *Annu. Rev. Biophys. Biomol. Struct.* 1997, 26, 541-66.
76. Salamon, Z.; Macleod, H. A.; Tollin, G. *Biophys. J.* 1997, 73, 2791-2797.
77. a) Salamon, Z.; Macleod, H. A.; Tollin, G. *Biochim. Biophys. Acta.* 1997, 1331, 117-129. b) Salamon, Z.; Macleod, H. A.; Tollin, G. *Biochim. Biophys. Acta.* 1997, 1331, 131-152.
78. Salamon, Z.; Brown, M. F.; Tollin, G. *Trends Biochem. Sci.* 1999, 24, 213-219.

The invention claimed is:

1. An amphipathic glycopeptide, the amino acid sequence of which comprises an N-terminal opioid message sequence, a C-terminal helical address sequence, and a linker sequence between the message sequence and the helical address sequence, wherein
   the C-terminal helical address sequence has a length of nine amino acids, and
   at least one of the amino acid residues of the peptide is glycosylated.

2. The glycopeptide of claim 1, wherein the N-terminal opioid message sequence is Y-t-G-F- or Y-a-G-F-.

3. The glycopeptide of claim 1, wherein the N-terminal opioid message sequence is Y-t-G-F-L-P-.

4. The glycopeptide of claim 1, wherein the N-terminal opioid message sequence is Y-t-G-F-L-βA-.

5. The glycopeptide of claim 1, wherein the N-terminal opioid message sequence is Y-t-G-F-L-G-G-.

6. The glycopeptide of claim 1, which is a glycosylated enkephalin.

7. The glycopeptide of claim 1, which is a glycosylated endorphin.

8. The glycopeptide of claim 1, which adopts a helical conformation in the presence of a lipid bilayer.

9. The glycopeptide of claim 1, which is substantially non-helical in water in the absence of a lipid bilayer.

10. The glycopeptide of claim 1, which is substantially non-helical in water in the absence of a lipid bilayer and adopts a helical conformation in the presence of a lipid bilayer.

11. The glycopeptide of claim 1, wherein one amino acid residue is glycosylated.

12. The glycopeptide of claim 1, wherein two amino acid residues are glycosylated.

13. The glycopeptide of claim 1, which comprises at least one serine residue that is glycosylated.

14. The glycopeptide of claim 1, which comprises 2 serine residues that are glycosylated.

15. The glycopeptide of claim 1, which is glycosylated with a glycosyl unit having at most 8 saccharide units.

16. The glycopeptide of claim 1, which is glycosylated with a glycosyl unit having at most 4 saccharide units.

17. The glycopeptide of claim 1, which is glycosylated with a glycosyl unit having at most 2 saccharide units.

18. The glycopeptide of claim 1, which is glycosylated with a glycosyl unit having at most 1 saccharide unit.

19. The glycopeptide of claim 1, which contains one serine glucoside residue.

20. The glycopeptide of claim 1, which contains 2 serine glucoside residues.

21. The glycopeptide of claim 1, which comprises at least 14 amino acid residues.

22. The glycopeptide of claim 1, which comprises at least 15 amino acid residues.

23. The glycopeptide of claim 1, which comprises at least 17 amino acid residues.

24. The glycopeptide of claim 1, which comprises at least 19 amino acid residues.

25. The glycopeptide of claim 1, which comprises at most 60 amino acid residues.

26. The glycopeptide of claim 1, which has at most 5% helicity as measured by circular dichroism in water and at least 10% helicity in the presence of a lipid bilayer.

27. The glycopeptide of claim 1, which crosses the blood-brain-barrier.

28. The glycopeptide of claim 1, which is selective for at least one receptor selected from the group consisting of the delta opioid receptor, mu opioid receptor and kappa opioid receptor.

29. A pharmaceutical composition comprising the glycopeptide of claim 1 and at least one pharmaceutically acceptable carrier and/or excipient.

30. A method of relieving pain, comprising administering an effective amount of the glycopeptide of claim 1 to a subject in need thereof.

31. A method of providing analgesia, comprising administering an effective amount of the glycopeptide of claim 1 to a subject in need thereof.

32. A method of treating anxiety, depression, obesity, anorexia nervosa, phobias, schizophrenia, Parkinson's disease or Alzheimer's disease, comprising administering an effective amount of the glycopeptide of claim 1 to a subject in need thereof.

* * * * *